United States Patent
Choe et al.

(10) Patent No.: US 7,473,426 B2
(45) Date of Patent: Jan. 6, 2009

(54) METHOD FOR SELECTIVELY INHIBITING REUPTAKE OF SEROTONIN AND NOREPINEPHRINE USING YEAST EXTRACT

(75) Inventors: Yun Seok Choe, 802-904 Hugokdongshin Apt. 1057, Ilsan3-dong, Ilsan-gu, Goyang-city, Kyungki-do (KR); Il Jun Kang, Chuncheon (KR); Hyung Joo Suh, Seoul (KR); Young Chun Choi, Chuncheon (KR); Hee Sun Yun, Seoul (KR); Kyung Mi Kim, Seoul (KR); Sang Wook Ahn, Seoul (KR); Ki Won Kim, Cheonju (KR); Won Jun Hwang, Incheon (KR); Jin Man Kim, Seoul (KR)

(73) Assignees: Yun Seok Choe (KR); Moon Sup Lee (KR)

( * ) Notice: Subject to any disclaimer, the term of this patent is extended or adjusted under 35 U.S.C. 154(b) by 270 days.

(21) Appl. No.: 11/141,497

(22) Filed: May 31, 2005

(65) Prior Publication Data

US 2006/0140974 A1 Jun. 29, 2006

Related U.S. Application Data

(63) Continuation-in-part of application No. 10/469,271, filed as application No. PCT/KR02/00324 on Feb. 27, 2002, now abandoned.

(30) Foreign Application Priority Data

Feb. 27, 2001 (KR) .................................. 2001-9946
May 14, 2001 (KR) .............................. 2001-26208
May 28, 2004 (KR) ...................... 10-2004-0038190

(51) Int. Cl.
  *A01N 63/04* (2006.01)
  *A61K 36/06* (2006.01)
(52) U.S. Cl. ............................... 424/195.16; 435/255.1
(58) Field of Classification Search ........................ None
See application file for complete search history.

(56) References Cited

U.S. PATENT DOCUMENTS 3,679,793 A * 7/1972 Cook et al. .................. 424/553

FOREIGN PATENT DOCUMENTS

| GB | 2225236 | 5/1990 |
| JP | 10265402 | 10/1998 |
| WO | 9602267 | 2/1996 |
| WO | 9702356 | 1/1997 |
| WO | 9708960 | 3/1997 |

OTHER PUBLICATIONS

Chakrabarty S et al. 2007. Fibromyalgia. American Family Physician 76: 247-254.*

Pae Cu et al. 2007. Extended-release formulation of venlafaxine in the treatment of post-traumatic stress disorder. Expert Rev Neurother 7: 603-615.*

Blackwell B et al. 1967. Hypertensive interactions between monoamine oxidase inhibitors and foodstuffs. Br J Psychiatry 113: 349-365.*

Thoenen, H., et al.; "Neurotrophic Factors"; Science; vol. 229; p. 238-242; 1985.

Sonavane, G.S., et al.; "Anxiogenic activity of Myristica fragrans seeds"; Pharmacology, Biochemistry and Behavior; vol. 71; pp. 247-252; 2002.

Rudnick, G., et al.; "Binding of the Cocaine Analog 2beta-[3H] Carboxymethoxy-3beta-(4-fluorophenyl)tropane to the Serotonin Transporter"; Molecular Pharmacology; vol. 40; pp. 421-426; 1991.

Rowland, N., et al.; "Neurobiology of an Anorectic Drug: Fenfluramine"; Progress in Neurobiology; vol. 27; pp. 13-62; 1986.

Nakamura, K., et al.; "Anxiolytic effects of aniracetam in three different mouse models of anxiety and the underlying mechanism"; European Journal of Pharmacology; vol. 420; pp. 33-43; 2001.

Deegenaars, M., et al.; "Heat Shock Response in the Thermophilic Enteric Yeast Arxiozyma telluris"; Applied and Environmental Microbiology; vol. 64, No. 8; pp. 3063-3065; Aug. 1998.

Masson, J., et al.; "Neurotransmitter Transporters in the Central Nervous System"; Pharmacology Reviews; vol. 51, No. 3; pp. 439-464; 1999.

Ljung, T., et al.; "Treatment of abdominally obese men with a serotonin reuptake inhibitor: a pilot study"; Journal of Internal Medicine; vol. 250; pp. 219-224; 2001.

Frazer, A., et al.; "New views of biogenic amine transporter function: implications for neuropsychopharmacology"; International Journal of Neuropsychopharmacology; vol. 2; pp. 305-320; 1999.

(Continued)

*Primary Examiner*—Lora E Barnhart
(74) *Attorney, Agent, or Firm*—Cantor Colburn LLP

(57) ABSTRACT

A yeast extract or yeast-derived bioactive peptide having an activity of selectively inhibiting reuptake of serotonin and norepinephrine, which can be effectively used in preventing or treating various diseases related to reuptake of serotonin and norepinephrine, especially depression, anxiety, stress, fatigue and obesity is provided. Also, a yeast extract or yeast-derived bioactive peptide having activities as an anti-stress agent, an anti-fatigue agent, premenstrual syndrome (PMS) and menstrual pain relaxants, and a brain-neurotrophic factor, and a method for preparing the bioactive peptide is provided. The yeast extract or yeast-derived bioactive peptide is effective in relieving stress, nervousness, anxiety, tension, insomnia, fatigue, and imbalance in the autonomic nerve regulation. Therefore, the yeast extract or yeast-derived bioactive peptide is available as an anti-depression agent, an anti-anxiety agent, an anti-stress agent, an anti-fatigue agent, an anti-obesity agent, premenstrual syndrome and menstrual pain relaxants, a brain-neurotrophin, and a source of active foods having these activities.

6 Claims, 12 Drawing Sheets

OTHER PUBLICATIONS

Barker, E., et al.; "Chimeric Human and Rat Serotonin Transporters Reveal Domains Involved in Recognition of Transporter Ligands"; Molecular Pharmacology; vol. 46; pp. 799-807; 1994.

Ashton, H.; "Benzodiazepine withdrawal: an unfinished story"; British Medical Journal; vol. 288; pp. 1135-1140; Apr. 14, 1984.

Ogilvie, A., et al.; "Polymorphism in serotonin transporter gene associated with susceptibility to major depression"; The Lancet; vol. 347; pp. 731-733; Mar. 16, 1996.

Pacher, P., et al.; "Current Trends in the Development of New Antidepressants"; Current Medicinal Chemistry; vol. 8; pp. 89-100; 2001.

Cherin, P., et al.; "Risk of Syncope in the Elderly and Consumption of Drugs: A Case-Control Study"; J. Clin. Epidemiol.; vol. 50, No. 3; pp. 313-320; 1997.

Masand, P., et al.; "Selective Serotonin-Reuptake Inhibitors: An Uptake"; Harvard Rev Psychiatry; vol. 7; pp. 69-84; 1999.

Longo, L., et al.; "Addiction: Part I. Benzodiazepines—Side Effects, Abuse Risk and Alternatives"; Am. Fam. Physician; vol. 61; pp. 2121-2128; 2000.

Corrodi, H., et al.; "The Effect of Immobilization Stress on the Activity of Central Monoamine Neurons"; Life Sciences; vol. 7; pp. 107-112; 1968.

Cook, E.H., et al.; "Evidence of linkage between the serotonin transporter and autistic disorder"; Molecular Psychiatry; vol. 2; pp. 247-250; 1997.

Lesch, K., et al.; "Association of Anxiety-Related Traits with a Polymorphism in the Serotonin Transporter Gene Regulatory Region"; Science, vol. 274, No. 5292; pp. 1527-1531; Nov. 29, 1996.

* cited by examiner

▨ HYDROPHOBIC FORCE (Van der Waals' force)

▨ HYDROPHOBIC FORCE

☐ HYDROPHOBIC BONDING

▨ IONIC BONDING

METHOD FOR SELECTIVELY INHIBITING REUPTAKE OF SEROTONIN AND NOREPINEPHRINE USING YEAST EXTRACT

CROSS-REFERENCE TO RELATED APPLICATIONS

This application claims priority to Korean Application No. 2004-38190, filed May 28, 2004, and is a continuation-in-part of U.S. application Ser. No. 10/469,271, filed Aug. 27, 2003, now abandoned, a U.S. national stage application of International Application No. PCT/KR02/00324, filed Feb. 27, 2002, which claims priority to Korean Application No. 2001-0026208, filed May 14, 2001, and to Korean Application No. 2001-0009946, filed Feb. 27, 2001.

BACKGROUND OF THE INVENTION

1. Field of the Invention

The present invention relates to a method for selectively inhibiting reuptake of serotonin and norepinephrine using yeast extract, in other words, a yeast extract or yeast-derived bioactive peptide having an activity of selectively inhibiting reuptake of serotonin and norepinephrine, which can be effectively used in preventing or treating various diseases related to reuptake of serotonin and norepinephrine, especially depression, anxiety, stress, fatigue and obesity. The yeast extract or yeast-derived bioactive peptide also has activities as an anti-stress agent, an anti-fatigue agent, premenstrual syndrome and menstrual pain relaxant, and a brain-neurotrophic factor.

2. Description of Related Art

Depression is one of the major psychiatric disorders. About 10% of world population has suffered from depression, of which the prevalence rate is increasing recently (Bland, 1997). Depression having symptoms to suppress emotion and reduce interest and pleasure can reduce efficiency of work and ability of logical communication of the patients and make the patients to commit suicide in serious case (Johnson et al., 1992).

There are several reasons for depression. As a biological reason, abnormality of neurotransmitter can induce a depression. Actually, action of brain such as our thought and emotion is understood to be generated by change of the neurotransmitter. Among them, depression is known to be generated by deficiency or hypofunction of serotonin and norepinephrine which are neurotransmitters connecting between nerves. Therefore, in order to treat the depression, a drug which can normalize or accumulate the said neurotransmitters should be administered.

In the brain, chemical signals are transferred by neurotransmitters derived from neurons. The neurotransmitters are secreted at a synapse in which signal transfer between neurons takes place. As shown in FIG. 1, the signal transfer can properly function when synthesis (1), secretion (2), receptor binding (3), reuptake (4) and degradation (5) of the neurotransmitter are balanced. If the reuptake is unduly excessive, the neurotransmitter becomes deficient.

As a conventional anti-depression drug used clinically, there are tri-cyclic antidepressants (TCAs), selective serotonin reuptake inhibitors (SSRIs), monoamine oxidase inhibitors (MAOIs) and indeterminate antidepressants (Atypicals). The TCAs can inhibit the transfer of amine transmitters (serotonin, norepinephrine, dopamine) to neural end. The SSRIs is a drug having a priority in treating depression (Masand Gupta, 1999), however, it was reported that administration of SSRI (fluoxetine) to an old person can induce apoplexy or orthostatic hypertension (Cherin et al., 1997). The TCAs and MAOIs can reinforce the activity of serotonin and norepinephrine and inhibit cholinic, histaminic, α-1-adrenalinic receptor regions. However, they can induce various side effects by reacting with many other drugs (Pacher et al., 2001).

Anxiety induces a confusion of emotion, thought, action and physical activity (Sonavane et al., 2002). The anxiety was reported to be generated by abnormal neuro-transfer of serotonin and dopamine (Nakamura et al., 2001). Benzodiazepine drug is a synthetic compound most frequently prescribed to treat anxiety or depression (Longo and Johnson, 2000). However, long-term administration of the benzodiaxepine drug can induce lowering of cognition (Rickels et al., 1983) and physical dependence and tolerance (Ashton, 1984).

Obesity is caused from breakage of balance of appetite control and metabolic control in the body. An important target for treating the obesity is to induce suppression of appetite by increase the level of brain serotonin which is one of the appetite suppressing neurotransmitter. If the secretion of serotonin is increased in the brain, the appetite is suppressed. This was found in the process of treating depression patient, where many depression patients administered with antidepressant increasing serotonin amount experience had experience of decreasing of appetite. Fenfluramine, dexfenfluramine and sibutramine which are prescribed to obesity patients have an activity to selectively inhibit reuptake of serotonin and norepinephrine in pre-synaptic neuron and therefore increase the level of serotonin in the synapse (Richard J et al., J Nutr Biochem 9, 511-515, 1998; Ljung, T et al., J of internal medicine 250(30), 219-224, 2001).

Modern peoples suffer from various types of daily stress. Emotional changes caused by such stress affect the autonomic nervous system, hormone secretion, and immune system in the human body and further ones' overall heath.

In general, when the human body is stressed, due to stimulation of the sympathetic part of the autonomic nervous system, secretion of hormones, in particular, adrenaline, is triggered (Corrodi H, Fuxe K, Hokfelt T.; The effect of immobilization stress on the activity of central monoaminergic neuron, Life Science 7: 108-112, 1968). To inhibit continuous stimulation of the sympathetic part, the parasympathetic part is spontaneously stimulated to secrete acetylcholine, and thus the body maintains balance in the autonomic nervous system. However, when the human body is subjected to excess stress for a long period of time, the body is too exhausted to effectively manage the stress accumulated in the sympathetic part, so balance in the autonomic nervous system is destroyed and directly affect the mechanisms of cellular and humoral immunity, thereby causing immunodeficiency, functional disorders. This abnormal state if it is prolonged causes organ disorders.

As a result, peptic ulcer, hypertension, cancer, diabetes, irritable colon syndrome, cardiopathy, bronchial asthma, tension headache, arthritis, neurodermatitis, etc. may result. Typical symptoms include liability to fatigue, impatience in daily life, inability to fall into a deep sleep, chills, sweating, shoulder pains, oppressed feeling, feeling as if something is in throat, dizziness, hyposexuality for males, and infertility for females.

To alleviate those stress disorder, conventionally, psychotropics have been used; for example, minor tranquillizers such as diazepam, meprobamate, methylpentinol, and etifoxine; neuroleptics such as chloropromazin, promethazine, and azapaerone; beta-adrenergic antagonist such as bunitrol; antidepressants such as a triple- or quadruple-ring compound, which are used alone or together with a neuropleptic; psycoanaleptics such as caffeine, amphetamine, or derivatives thereof; and sedatives and hypnotics such as a phenobarbital-codeine complex (Poldinger, W., Schmidlin, P. E., Wider, F., Index Psychopharmacorum, H. Buber, Bern). However, the use of those psychotropics relies on pharmacotherapy for relief of a predominant symptom without pathological consideration of the cause of the stress and cannot reduce chromatic damages caused from the stress. Also, the psychotropics cannot resist the stress through catabolic regeneration but rather inhibits a normal reaction in that body is adapted to stress and causes a number of adverse effects. Typically, Human body develops tolerance to the antianxiety agents and psychoanaleptics such as amphetamine or caffeine and thus dosage of above drugs need to be increased. A significant adverse effect is that there is the probability of becoming dependent on the psychoactive agent.

To eliminate such imbalance in the autonomic nervous system due to stress, many attempts have been made in a variety of aspects. In particular, stress is medically defined as a negative stimulus destructing the body's homeostasis. Neurotransmitters are involved in the negative stimulus. Acetylcholine derived from cholesterol, described above, is an important neurotransmitter. Acetylcholine, a relaxation-inducing neurotransmitter, is secreted from the parasympathetic part of the autonomic nervous system. About 50 other neurotransmitters have been discovered so far.

Such a neurotransmitter needs a complementary counterpart called a "receptor" for it to function. Although a number of neurotransmitters exist, the neurotransmitters cannot function properly if there is no receptor having a peptide structure to be coupled to the neurotransmitter. A muscarinic receptor, which is coupled to acetylcholine, is composed of peptides including aspartic and glutamic residues, which are important for the coupling, and hydrophobic amino acids surrounding the residues (Gearien 1999). When a neurotrophic factor including these peptides is supplied to the body, nerve cells are nourished and grown to treat a variety of neuropathies, such as Parkinson's disease, without side effects. By accelerating the generation of sufficient neurotransmitters and their receptors, impulses on nervous system by excess stress (stimuli) can be absorbed and delivered without causing a load to the nerve cells, thereby treating stress disorders. In other words, to intensify the nervous system, it is important to take in peptides acting as a neurotrophic factor to generate neurotransmitter receptors as well as neurotransmitters themselves. Since receptor peptides react depending on the amount of neurotransmitters, there is no side effect due to the excess dose of the receptor peptide.

A "brain-neurotrophic factor" refers to a neurotrophin for nerve tissues, such as the brain and spinal marrow, to accelerate the growth of the nerve cells or neuroglia cells. In the past, it was believed that brain nerve cells could not be grown. However, since then it has been discovered that brain nerve cells grow and proliferate with the supply of a particular neurotrophic factor and interest in studying neurotrophins has been increased. Accordingly, neurotrophins to regulate the growth and proliferation of nerve cells and their peptide sequences have been discovered with fetal and animal brains. Neurotrophins having peptides capable of accelerating the growth and proliferation of the nerve cells or neuroglia cells have been known to be effective for the treatment of functional disorders caused from nerve cell degeneration, such as Parkinson's disease and Alzheimer's disease (Varon and Bunge 1997, Ann. Rev. Neuroscicence 1:327; Thoenen and Edgar 1985, Science 229:238).

Significant neurotrophic factors found to date, include nerve growth factor (NGF), brain-derived neurotrophic factor (BDNF), glial cell-derived neurotrophic factor (GDNF), Neurotrophin-3 (NT-3), NT-4/5, etc., which are kinds of peptides. However, use of a human or fetal brain to find a new neurotrophic factor raises ethical issues, because it is extracted from a corpus, and the amount of neurotrophic factor is too trace to be detected in the brain. So, only a few neurotrophic factors have been found up to now. Therefore, many kinds of neurotrophic factors, more than those identified to date, are predicted to exist.

Conventionally, a neurotrophic factor or neurotransmitter has been obtained by preparing a synthetic peptide or recombinant peptide using a peptide synthesizer or a genetic recombinant technique through polymerization chain reaction (PCR), respectively. However, these techniques are costly and cause a safety problem, thereby limiting commercial applications. Most synthetic or recombinant peptides are macromolecules of 30,000 daltons or greater, so they cannot pass through a brain blood barrier and reach a brain nerve cell through a brain blood barrier by oral administration, and thus direct injection into the brain is necessary (Medical Report 1998, Editions of Jan. and Feb.).

Therefore, it would be desirable to prepare a neurotropic peptide, using a yeast extract or yeast peptide derived from a food-grade yeast as in the present invention, having anti-stress, anti-fatigue, anti-anxiety, and deep sleep-inducing effects with a comparatively small dose, without using complicated processes of the genetic recombination method. This neurotropic peptide derived from the yeast according to the present invention can be widely applied for commercial use, compared to conventional neurotropic factors (Neurotrphin, NT-3, BDNF, NGF, etc.) identified by genetic recombination and does not cause a safety problem, such as suspicion of a genetic mutant.

Yeast, generally recognized as safe (GRAS) for the human body, contains 50% or more quality proteins, excess minerals, vitamin B, etc., so it has been widely used in the liquor or bakery industry as a source of protein, nucleic acids, enzymes, liquids, vitamins, minerals, etc. (Roman et al., Food Biotechnology, 6, 225, 1992). Yeast extracts produced by autolytic enzyme or other proteases have been used as a source of microorganism fermentation media, seasonings, and health foods (Bioindustry, 14, 53, 1997). However, the functionality of the yeast extract hydrolyzed from yeast or yeast-derived peptides and their specific use as an anti-stress agent and a native brain-neurotrophic factor through experimental assays have not been reported yet. Also, the production of anti-stress and anti-anxiety agents, sleeping drugs, and other medicines using the yeast-derived peptides has not been disclosed. In addition, the effect of the yeast extract on premenstrual syndromes similar to stress symptoms or on menstrual pains is not known.

Premenstrual syndromes (PMS) refer to symptoms experienced by fertile women during their menstrual cycle after ovulation, including physical symptoms such as cramp pain, low back pain, peycalgia, abdominal bloating, diarrhea, constipation, and breast fullness and tenderness, and emotional symptoms such as anxiety, irritability, depression, insomnia, fatigue, reduction in concentration, idioctonia impulse, etc. Those symptoms are similar to stress symptoms and are experienced by 70% of all women, unendurable to 20% of those women, thereby causing social and economical losses due to the inability to work.

Menstrual pains refer to mild or incapacitating cramp pains or low back pain generally experienced by most women, about 50% of all fertile women, combined with PMS before, after, or during their menstrual cycle. Mostly, young women within 1 or 2 years after their menarche suffer from menstrual pains, but this may be sustained into their forties. Reportedly, about 10% of those feels so painful not to able to ordinary work for 1 to 3 days a month. According to the result of a survey by Kyunghee University Oriental Medicine Hospital, 47% suffered from menstrual cramp pain, low back pain, and more seriously, headaches, during their menstrual cycle, 13% experienced disturbance gastrointestinal such as anorexia and indigestion, and 8% had disesthesia. In particular, about 70% of 632 middle and high school girls, 50% of those seriously, experienced menstrual pains. Such serious symptoms for the students are believed to be due to stress from excess schoolwork and examination. It was also investigated that above 90% of those basically do not manage their pain, 66% of those endure the pain without any treatment, and 28% of those take analgesics.

In spite of the efforts made by many researchers over a long period of time, the causes of PMS or menstrual pains have not been accurately identified yet. The relevancy of incretory hormonal imbalance during menstrual cycle to PMS or menstrual pains has been perceived.

There are several pathogeneses for PMS and menstrual pains. The pathogeneses may include considering those arising from the deficiency of progesterone, the excess secretion of estrogen and androgen, the excess secretion of pain-inducing prostaglandin, or the deficiency of vitamin B complex or essential fatty acids. In general, it is believed that PMS or menstrual pains occur due to the combination of the above-listed factors together with an environmental factor.

According to the most convincing pathogenesis for PMS and menstrual pains related with the excess secretion of prostaglandin, in the female menstrual cycle, as the secretion of a luteinizing hormone (LH), progesterone, stops, the pain inducing prostaglandin is secreted. As a result, tunica myometrium is contracted, and transient anemia and menstrual pains occur. According to this theory, to suppress such PMS or pains, the following methods have been suggested.

As a most widely used method, the production of prostaglandin is suppressed with the administration of, for example, aspirin or ibuprofen to relieve the menstrual pains. In another method, an anti-anxiety agent or anti-depressant, such as benzodiazepine, is used. Alternatively, progesterone is administered in the luteinizing phase of the female menstrual cycle.

In another treatment method, Korean Patent No. 0171408 discloses the use of melatonin (N-aceryl-5-methoxytryptamine), and Korean Laid-open Application No. 2001-0024462 discloses the use of serotonin (5-hydroxytryptamine).

Among a number of methods for treatment of PMS or menstrual pains, treatments with hormones, such as progesterone, melatonin, or serotonin, or with neurotransmitters in the luteinizing phase are known to be effective for relieving general pains, stress, chronic fatigue, and depression as well as PMS or menstrual pains.

However, those treatment methods of direct administration of hormones, such as melatonin or serotonin, cannot ensure 100% safety, and the cost of preparing the pharmaceuticals is high. Therefore, the treatment agents are not generally taken.

Yeast is known to respond sensitively to external conditions, compared to other microorganisms. Yeast has the ability to grow in both anaerobic and aerobic conditions, stops growing if the condition of a growth medium is unsuitable for growth, and undergoes heterozygosis to sustain itself under poor external environments. All organisms exhibit an alarm reaction when a stress is perceived for the first time and actively resists against the stress if the stress is not relieved to induce physiological changes for homeostasis (Seyle, 1956).

The inventor has realized the present invention by combining the above characteristics of yeast and organisms. In particular, after full proliferation of yeast, the growth medium was subjected to physical and chemical stresses, such as high-temperature heating, ultrasonic waves or vibrations, and pH variations, of a degree not to causing destruction, to produce excess anti-stress substances such as proteins and enzymes. A yeast extract was prepared by autolysis or hydrolysis with a protease, and purified by ultrafiltration to attain yeast-derived peptides. Also, it was proven that the yeast extract and peptides have activities as brain-neurotrophins (derived from the natural source), therapeutic and prophylactic agents for the treatment of autonomic nerve disorders, such as an anti-stress agent, anti-anxiety agent, or sleeping aids, and PMS and menstrual pain relaxants, the PMS and menstrual pains showing similar symptoms to stress.

SUMMARY OF THE INVENTION

The present invention provides a new use of yeast extract and bioactive peptides obtained by hydrolyzing yeast as an selective serotonin and norepinephrine reuptake inhibitor.

The present invention provides a new use of yeast and bioactive peptides obtained by hydrolyzing yeast extract as an anti-depression agent to treat depression caused from undue reuptake of serotonin and norepinephrine.

The present invention provides a new use of yeast extract and bioactive peptides obtained by hydrolyzing yeast as an anti-anxiety agent to treat anxiety caused from undue reuptake of serotonin and norepinephrine.

The present invention provides a new use of yeast extract and bioactive peptides obtained by hydrolyzing yeast as an anti-stress agent to treat stress caused from undue reuptake of serotonin and norepinephrine.

The present invention provides a new use of yeast extract and bioactive peptides obtained by hydrolyzing yeast as an anti-fatigue agent to recover fatigue caused from stress or muscular fatigue caused from exercises.

The present invention provides a new use of yeast extract and bioactive peptides obtained by hydrolyzing yeast as an anti-obesity agent to treat obesity caused from undue reuptake of serotonin and norepinephrine.

The present invention provides a new use of yeast extract and bioactive peptides obtained by hydrolyzing yeast as a natural brain-neurotrophin to treat stress disorders and maintain balance in the human autonomic nervous system.

The present invention provides a new use of yeast extract and bioactive peptides obtained by hydrolyzing yeast as premenstrual syndrome and menstrual pain relaxants to reduce premenstrual syndromes (PMS) and menstrual pains similar to symptoms from stress and chronic fatigue.

The present invention provides a functional beverage, functional gum or functional edible film containing a yeast extract or bioactive peptides obtained by hydrolyzing yeast as an active component having activities as an anti-depression agent, an anti-anxiety agent, an anti-stress agent, an anti-fatigue agent, anti-obesity agent, premenstrual syndrome and menstrual pain relaxants and a sleeping aids to treat neurogenic disorder, especially imbalance in the autonomic nervous system, caused from stress.

In accordance with an aspect of the present invention, there is provided a method for selectively inhibiting reuptake of serotonin and norepinephrine comprising administering an effective amount of a yeast extract. In the present invention, the term "yeast extract" is understood to include a crude yeast extract, a purified yeast extract and bioactive peptides obtained by hydrolyzing yeast.

In the present method, the yeast extract may be prepared using conventional extraction methods, for example by culturing yeasts, recovering the cultured yeast with centrifugation and hydrolyzing the recovered yeast. Preferably, the hydrolyzing step can be carried out by autolyzing the recovered yeast at a temperature of about 35-70° C. and/or hydrolyzing with a protease.

In the present method, the yeast extract may be used for preventing or treating a disease related to reuptake of serotonin and norepinephrine. In the present invention, the disease related to reuptake of serotonin and norepinephrine include any disease which is induced by deficiency or hypofunction of serotonin and norepinephrine caused from undue reuptake of them, for example depression, anxiety, stress, fatigue, obesity and the like.

In accordance with an aspect of the present invention, there is provided a method for reduce or relax premenstrual syndromes (PMS) and menstrual pains.

In the present method, the yeast extract is administered in form of a pharmaceutical composition or a functional food comprising the yeast extract as an active component, preferably a functional beverage, a functional gum or functional edible film.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
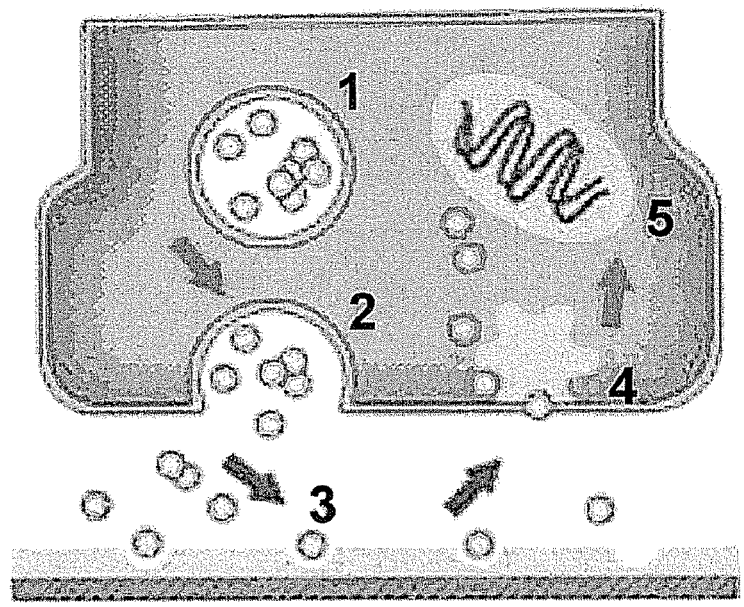
FIG. 1 is a schematic drawing depicting the process of reuptake of neurotransmitters (serotonin or norepinephrine) in the synapse.

Hereinafter, the present invention will be described in greater detail.

In accordance with an aspect of the present invention, there is provided a yeast extract derived from yeast and having activities as an anti-depression agent, an anti-anxiety agent, an anti-stress agent, an anti-fatigue agent, an anti-obesity agent, premenstrual syndrome and menstrual pain relaxants, and a neurotrophic factor.

In the yeast extract according to the present invention, the source yeast contains excess high-quality proteins, minerals, and B vitamins. The yeast extract is obtained by known general extractions methods, for example, using an autolytic enzyme or protease. Commercially available yeast extracts were found to have activities as an anti-depression agent, an anti-anxiety agent, an anti-stress agent, an anti-fatigue agent, an anti-obesity agent, PMS and menstrual pain relaxants, and a brain-neurotrophic factor, like the yeast extract according to the present invention.

The yeast extract according to the preset invention having activities as an anti-depression agent, an anti-anxiety agent, an anti-stress agent, an anti-fatigue agent, an anti-obesity agent, premenstrual syndrome and menstrual pain relaxants, and a neurotrophic factor, is prepared by autolyzing the yeast preferably at a temperature of about 35-70° C., and more preferably, a temperature of about 50-60° C.

Only with the autolysis at a high temperature greater than or equal to about 35° C., an effective anti-stress activity can be induced to the yeast extract. It is believed that heating the yeast simultaneously triggers the release of stress-resistant substances to provide an anti-stress effect during autolysis. Alternatively, by applying an additional stress such as ultrasonic waves or vibrations, a new strain of yeast with enhanced stress resistance can be screened. The anti-stress activity of the yeast extract according to the present invention can be further improved by repeatedly applying such stresses to enhance the release of stress-resistant substances.

In the yeast extract according to the preset invention having activities as an anti-depression agent, an anti-anxiety agent, an anti-stress agent, an anti-fatigue agent, an anti-obesity agent, premenstrual syndrome and menstrual pain relaxants, and a neurotrophic factor, it is preferable that the yeast is hydrolyzed with a protease during or after the autolysis. According to this invention, only a supernatant obtained by centrifuging hydrolytes produced in the hydrolysis may be included in the yeast extract according to the present invention having activities as an anti-depression agent, an anti-anxiety agent, an anti-stress agent, an anti-fatigue agent, an anti-obesity agent, premenstrual syndrome and menstrual pain relaxants, and a neurotrophic factor.

Also, the present invention provides a yeast-derived peptide having activities as an anti-depression agent, an anti-anxiety agent, an anti-stress agent, an anti-fatigue agent, an anti-obesity agent, premenstrual syndrome and menstrual pain relaxants, and a neurotrophic factor, the yeast-derived peptide characterized by including molecules of 10,000 daltons or less obtained by ultrafiltrating the supernatant from the centrifugation performed in the above preparation of the yeast extract according to the present invention.

In the yeast-derived peptide according to the present invention, the molecular weight cutoff value of 10,000 was determined by considering a variety of activities of peptides as an active food source to regulate body functions (New Technology Trend Report of 2000, Active Food, Korean Industrial Property Office). In general, molecules of a molecular weight of 10,000 or less are called "peptides". The brain has a brain blood barrier which blocks macromolecules of a molecular weight of 15,000 or greater to protect the cerebrovascular system. Therefore, the yeast-derived peptide according to the present invention having a molecular weight of 10,000 or less can easily pass through the brain blood barrier.

Alternatively, a yeast-derived peptide according to the present invention having activities as an anti-depression agent, an anti-anxiety agent, an anti-stress agent, an anti-fatigue agent, an anti-obesity agent, premenstrual syndrome and menstrual pain relaxants, and a neurotrophic factor is characterized by comprising glutamic acid and aspartic acid of about 15-25 mol % each.

Since the yeast-derived peptide according to the present invention is rich in glutamic acid and aspartic acid, which are amino acids involved in the synthesis of muscarinic acetylcholine receptors, it is effective in alleviating stress disorders caused by the imbalance in the autonomic nervous system, including PMS and menstrual pains.

In accordance with another aspect of the present invention, there is provided a method for preparing a yeast extract having activities as an anti-depression agent, an anti-anxiety agent, an anti-stress agent, an anti-fatigue agent, an anti-obesity agent, premenstrual syndrome and menstrual pain relaxants, and a neurotrophic factor, the method comprising: incubating a strain of yeast until a maximum growth phase; inducing autolysis of the yeast at a temperature of about 35-70° C. and simultaneously hydrolyzing the yeast with an addition of a protease; and attaining a supernatant by centrifuging the hydrolytes from the yeast.

Alternatively, the method for preparing the yeast extract according to the present invention may further comprise screening a new strain of the yeast survived resisting to stress by heating at high-temperature, applying ultrasonic waves and vibrations, and changing pH to a degree not to cause destruction before the incubation until the maximum proliferation stage.

Alternatively, the method for preparing the yeast extract according to the present invention may further comprise inducing secretion of metabolites resistant to stress by applying a physical or chemical stress selected from the group consisting of high-temperature heating, ultrasonic waves, vibrations, and pH variations, to a degree not to cause destruction before the autolysis.

This is based on the fact all organisms exhibit an alarm reaction when a stress is perceived for the first time and actively resists against the stress if the stress is not relieved to induce physiological changes for homeostasis (Seyle, 1956). In other words, when yeast is subjected to stress, it secretes a variety of enzymes to resist against the stress. The released enzymes are low molecular weight proteins having an activity as a neurotrophic factor to relieve the human body of the stress. Based on this fact, the yeast extract preparation method according to the present invention has been realized.

Physical or chemical stimuli applied to yeast in the preparation of a yeast extract according to the present invention to induce the generation and release of anti-stress substances from the yeast include heating at a temperature of about 35-45° C. which is higher than the optimum growth temperature of the yeast, ultrasonic waves, vibrations, and pH variations, to a degree not to destroying the yeast.

Preferably, the method for preparing the yeast extract according to the present invention comprises: screening a new strain of yeast resistant to stress by incubating the yeast with applications of ultrasonic waves and vibrations; inoculating the screened strain of the yeast on YM medium, incubating the medium at a temperature of about 22-25° C. until its exponential growth phase, collecting the yeast cells by centrifugation, and diluting the collected cells with a 1%-peptone buffer; applying ultrasonic waves and vibrations to the dilute at a high temperature of about 33-45° C. as stresses for 8 hours to induce the generation and release of stress-resistant metabolites from the yeast; autolysing the yeast product at a temperature of about 50-60° C. and simultaneously hydrolyzing the yeast product with the addition of a protease; and centrifuging hydrolytes to obtain a supernatant.

In accordance with another aspect of the present invention, there is provided a method for preparing a yeast-derived peptide having activities as an anti-depression agent, an anti-anxiety agent, an anti-stress agent, an anti-fatigue agent, an anti-obesity agent, premenstrual syndrome and menstrual pain relaxants, and a neurotrophic factor, the method characterized by comprising obtaining peptides only having a molecular weight of 10,000 daltons or less by ultrafiltrating the supernatant from the centrifugation in the preparation of the yeast extract according to the present invention.

According to the present invention, only low molecular weight yeast-derived peptides of 10,000 or less is selected by ultrafiltrating the supernatant from the centrifugation described above through a membrane having a molecular weight cutoff value of 10,000. As a result, substances that would drop the efficacy of the yeast extract are removed while the low molecular weight substances capable of easily being absorbed into the body and capable of passing through the brain blood barrier with high bioavailability are separated and purified.

Alternatively, the method for preparing the yeast extract or the yeast-derived peptide according to the present invention may further involve drying and grinding the yeast extract or the yeast-derive peptide.

In accordance with another aspect of the present invention, there is provided an anti-stress agent comprising the yeast extract or the yeast-derived peptide prepared by any of the above-described methods according to the present invention as an active component.

The anti-stress agent according to the present invention has an activity as a tranquilizer, a relaxant, an anti-anxiety agent, or a sleeping aids, and is effective in alleviating PMS and menstrual pains.

In accordance with another aspect of the present invention, there is provided an anti-fatigue agent (fatigue recovering agent) comprising the yeast extract or the yeast-derived peptide prepared by any of the above-described methods according to the present invention as an active component.

In accordance with another aspect of the present invention, there is provided a neurotrophin (neurotrophic factor) comprising the yeast extract or the yeast-derived peptide prepared by any of the above-described methods according to the present invention as an active component.

The present invention also provide a PMS and menstrual pain relaxant composition comprising the yeast extract or the yeast-derived peptide prepared by any of the above-described methods according to the present invention as an active component.

Preferably, the PMS and menstrual pain relaxant composition according to the present invention comprises: about 10-90% by weight dried powder of the yeast extract or the yeast-derived peptide; about 5-80% by weight chitosan; and about 5-80% by weight herbal powder of 5-80% by weight, based on the total weight of the premenstrual syndrome and menstrual pain relaxant composition. In this case, the chitosan may be a water-soluble macromolecule of a molecular weight greater than or equal to about 300,000. Preferably, the herbal powder is derived from at least one selected from the group consisting of Korean angelica root, Salviae Radix, *Curcuma aromatica*, Zedoariae Rhizoma, mint, liquorice, ginger, *Gastrodia*, white *Atractylis, Cnidium officinale*, cinnamon, and ginseng.

The functional food according to present invention can be prepared by using conventional method well known to food industry. For example, the functional food can be prepared in the forms of tablet, capsule, powder, granule, solution, pellet and the like. Preferably, the functional food can be prepared in the forms of functional beverage, functional gum and edible films.

In accordance with another aspect of the present invention, there is provided an active beverage having activities as an anti-depression agent, an anti-anxiety agent, an anti-stress agent, an anti-fatigue agent, an anti-obesity agent, premenstrual syndrome and menstrual pain relaxants, and a neurotrophic factor, the active beverage comprising the yeast extract or the yeast-derived peptide prepared by any of the above-described methods according to the present invention.

The yeast extract or yeast-derived peptide contained in the active beverage according to the present invention contains anti-stress substances released by applying stress to yeast recognized as safe. Therefore, the active beverage prepared using the yeast extract or yeast-derive peptide according to the present invention provides an anti-stress effect as a tranquilizer, a relaxant, a sleeping drug, etc., and can be conveniently taken without concern about any side effect.

Preferably, the active beverage according to the present invention comprises: about 0.1-10% by weight the yeast extract or the yeast-derived peptide by any of the above-described methods according to the present invention; about 10-25% by weight common additives for beverage including a sweeter and an acidulant, based on the total weight of the bioactive beverage; and the balance water.

In the present invention, the common additives for beverage include liquid fructose, sucrose, maltodextrin, glucose, citric acid, nicotinamide, pantothenic acid, sodium benzoate, and kinds of flavors. Preferably, in the preparation of the bioactive beverage according to the present invention, any fruit juice, for example, ume juice, is added.

The present invention also provides a method for preparing an bioactive beverage having activities as an anti-stress agent, an anti-fatigue agent, premenstrual syndrome and menstrual pain relaxants, and a neurotrophic factor, the method comprising: incubating a strain of yeast until a maximum growth phase; inducing autolysis of the yeast at a temperature of about 35-70° C. and simultaneously hydrolyzing the yeast with an addition of a protease; attaining a supernatant by centrifuging hydrolytes produced in the hydrolysis; mixing the supernatant with active carbon in water and sterilizing the mixture under pressure; and purifying the sterilized mixture until it loses its color by filtering the sterilized mixture with suction.

In preparing a beverage with the yeast extract containing anti-stress substances, purification is necessary to remove the yeast odor. For the purification, after mixing the prepared yeast extract with active carbon and water, the mixture is sterilized under pressure and filtered. Active carbon almost not adsorbs amino acid (Hyung-ik Song and Jung-yeub Shin, Contemporary Fermentation Engineering, 1998, 293). Based on this nature of active carbon, the yeast extract was mixed with active carbon for decolorization and deodorization in the present invention.

The active beverage according to the present invention having activities as an anti-stress agent, an anti-fatigue agent, premenstrual syndrome and menstrual pain relaxants, and a neurotrophic factor, is prepared by diluting the beverage concentrate after the filtering. An bioactive beverage according to the present invention can be prepared by any general beverage preparation method without limitation, as long as the yeast extract prepared by any of the methods described above according to the present invention is incorporated therein.

Preferably, the active beverage preparation method according to the present invention further comprises: screening a new strain of yeast survived resisting to stress by heating at high-temperature, applying ultrasonic waves and vibrations, and changing pH during incubation to a degree not to causing destruction; and inducing secretion of metabolites resistant to stress by applying a physical or chemical stress selected from the group consisting of high-temperature heating, ultrasonic waves, vibrations, and pH variations, to a degree not to causing destruction.

In the preparation of the bioactive beverage according to the present invention, it is preferable that the autolysis is performed at a temperature of about 50-60° C., and the pressure sterilization is performed at about 1.5 atm and a temperature of about 100-125° C. for about 10-15 minutes.

The functional gum according to the present invention can be prepared by conventional methods for preparing chewing gum, preferably by mixing and dissolving 50-65% by weight saccharide, 10-25% by weight sugar alcohol, 0.05-0.5% by weight citric acid, 0.01-0.05% by weight aspartame and 0.1-10% by weight the present yeast extract, adding and dissolving 20-40% by weight chewing base, adding and mixing 1-2% by weight fruits or herb fragrant powder, and heating and rolling to cast a chewing gum.

The edible film according to the present invention can be prepared by conventional methods for preparing edible film, preferably by preparing aqueous solution of polyhydric alcohol comprising polyhydric alcohol and water in a range of 0.2:99.8 to 20:80 weight ratio, dissolving water-soluble polysaccharide such as starch or pulluran and the present yeast extract, casting the resulting solution into a film, and drying the film to 25% by weight or less of water content. The edible film of the present invention can be heat-seamed and dissolved in hot bath, so can be used as materials of various food packaging bag.

Figure 2:
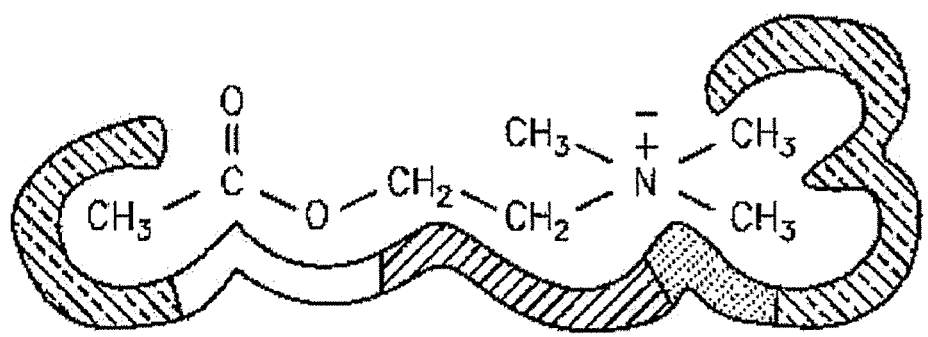
FIG. 2 is an illustration of a muscarinic acetylcholine receptor map.

To recover the human organs subjected to sustained stimulation of the sympathetic part due to stress, which causes imbalance in the autonomic nervous system, the parasympathetic part needs to be actively stimulated. To this end, there is a need to accelerate release of the neurotransmitter acetylcholine at synapses. In addition, acetylcholine receptors are necessary to efficiently deliver the released acetylcholine to neurons. Acetylcholine is bound to muscarinic receptors, as shown in FIG. 2. The presence of more muscarinic receptors in the synapsis results in more efficient transmission of acetylcholine. Therefore, more muscarinic receptors need to be synthesized. The muscarinic receptors are composed of seven fractions of protein and are believed to have a negatively charged site to couple with quaternary ammonium salt of acetylcholine significant for the muscarinic activity. The negatively charged site is considered to be derived from acidic amino acid residues, such as aspartic acid and glutamic acid (Keun-il Kang, 1992, Introduction to Medicinal Chemistry)

Therefore, peptide drugs enriched with acidic amino acids, aspartic acid and glutamic acid, to be used as a source material for the muscarinic acetylcholine receptors facilitates the biosynthesis of the muscarinic receptors in the human body and affects efficient transmission of acethylcholine of the parasympathetic part, thereby recover the imbalance in the autonomic nervous system due to the excess stimulation of the sympathetic part. As a result, the pathological conditions, both physical and emotional, caused from stress can be fundamentally inhibited or relieved.

The inventor has found that yeast extract is rich in amino acids effective in synthesizing the muscarinic receptors described above and can be effective in treating stress disorders caused from the imbalance in the nervous system.

A yeast extract according to the present invention is found to contain 18 kinds of amino acids with a great amount of aspartic acid and glutamic acid, which will be described later in Example 4. Aspartic acid and glutamic acid have a negatively charged R group. In other words, the result means that the yeast extract containing a large amount of negatively charged amino acids, which are essential to synthesis muscarinic receptors in the body, is a good source for the biosynthesis of the neurotransmitter acetylcholine distributed in the nervous system, including the parasympathetic part. Since the yeast extract according to the present invention accelerates transmission of the neurotransmitter at the parasympathetic part when the sympathetic part is excessively stimulated due to stress, the yeast extract according to the present invention has an activity as an anti-stress agent. Furthermore, the yeast extract according to the present invention can effectively relax premenstrual syndrome (PMS) and menstrual pains, which are similar to the symptoms from stress.

Food-grade yeast, generally recognized as safe (GRAS), contains 50% or greater quality protein, a large amount of minerals, and vitamin B complex. The yeast is rich in peptides as a source for the synthesis of neurotransmitters or their receptors, as described above. In particular, vitamin B and minerals contained in yeast are involved in general energy metabolism and activating the brain and neurons. Vitamin B6 (pyridoxine) is an essential nutrient for synthesizing neurotransmitters, including serotonin, dopamine, norepinephrine, gamma-amino butyric acid (GABA), and taurine. A deficiency of vitamine B6 causes dysthesia, anxiety, reduction in concentration, and hypomnesis. A deficiency of Vitamin B1 (thiamine) causes Korsakoff's syndromes such as weakness of memory, anaesthesia, and dementia. Vitamin B2 (riboflavin) acts as a coenzyme for the brain growth to be considered neurologically as an important neurotrophic factor.

In women with PMS or incapacitating menstrual pains, signs of progesterone deficiency, estrogen/progesterone imbalance, salt/water retention, prostaglandin deficiency or excess, prolactine excess, vitamin B6 (pyridoxine) deficiency, hypoglycemia, serotonin deficiency, etc. are observed. However, since the yeast extract according to the present invention contains a variety of amino acids, excess B vitamins, including B6, and excess minerals such as calcium and magnesium, hormone balance and metabolism activation are accelerated as those components are absorbed into the body, thereby rapidly reduce PMS and menstrual pains.

Furthermore, yeast contains comparatively excess selenium, which is essential to grow cranial nerve cells and to generate antioxidases. Deficiency of selenium results in depression and anxiety due to encephalopathy. Mineral enriched yeast, as an easily absorbable mineral supplement in the form of organically bound, chelated with minerals, such as selenium and chromium, is disclosed (U.S. Pat. No. 4,530, 846 issued on Jul. 23, 1985, entitled "Method for the Production of Selenium Yeast"). In view of the description above, yeast is considered to be applicable as a bioactive food material and natural peptide source in the form of yeast extract or yeast-derived peptides with an activity as a good brain-neurotrophic factor capable of relaxing stress, anxiety, excitation, somnipathy due to stress, and fatigue.

In the present invention, a variety of excess exoenzymes produced are secreted through the cell wall of the yeast. Therefore, the exoenzymes are low molecular weight proteins, which are enough small to pass the yeast cell wall. Therefore, the exoenzymes can act as a brain-neurotrophic factor capable of easily passing through the brain blood barrier in the human body.

When the growth conditions, such as temperature, pH, and nutrient composition and amount, are extremely undesirable, yeast is autolysed by its own enzyme to hydrolyze the cytoplasm and subsequently destruct the cell wall so that the hydrolyzed cytoplasm comes out of the cell. Due to the yeast autolysis, bioavailability of the yeast can be enhanced. By autolysing yeast after generation of excess low molecular weight anti-stress substances in the yeast, yeast-derived peptides containing a variety of proteins, minerals, and B vitamins, which are extracted from the yeast by the autolysis and act as effective neurotrophic factors, can be obtained.

The effect of yeast extract in relaxing stress and fatigue as a neurotrophic factor has been described above. Hereinafter, the effect of relaxing PMS and menstrual pains will be described in greater detail.

First, the yeast extract contains excess choline as a complex with vitamin B. Choline is a precursor of the relaxant neurotransmitter acetylcholine. Therefore, muscular tension and pain due to uterine contraction during menstruation can be alleviated by increasing choline intake.

Choline exists in a variety of forms. Among many types of choline, salicylic choline has a pain alleviating effect similar to aspirin and thus may be effective in alleviating menstrual pains. Although the cause of menstrual pains has not been identified accurately, it is expected due to excess secretion of prostaglandin during menstruation, which is observed in women with menstrual pains. Analgesia such as acetylsalicylic acid (aspirin) or ibuprofen inhibits the synthesis of prostaglandin to reduce prostaglandin secretion. As a result, neurotransmission of the pain is inhibited to be less painful.

Second, vitamin B6 in the yeast extract composition is very important in the synthesis and metabolism of amino acids and proteins, functions as a cofactor for the synthesis of red blood cells and antibodies, and is involved in the synthesis of a variety of neurotransmitters. Deficiency of vitamin B6 results in anemia, dermatitis, neuropathy, and cramp. Also, vitamin B6 is known to be essential to relieve PMS and menstrual pains.

Third, niacin in the yeast extract composition is involved in the enzymatic reaction for the synthesis of coenzymes, NAD (nicotinamide adenine dinucleotide) and NADP (nicotinamide adenine dinucleotide phosphate). These coenzymes are known to accelerate energy generation in the intracellular mitochondria and to activate the function of brain cells to treat schizophrenia. Accordingly, niacin can be effectively used to alleviate the psychological syndromes of PMS.

Niacin is one of metabolites of the essential amino acid tryptophan. Tryptophan is a precursor of serotonin widely used to relieve PMS and menstrual pains. Accordingly, the yeast extract containing an excess of tryptophan and niacin is obviously effective in relaxing PMS and menstrual pains. The presence of excess niacin structurally similar to serotonin, which is a kind of neurotransmitter synthesized in the body, indicates high likelihood of converting into serotonin and thus optimizes the autoregulation mechanism in the body to treat pain, chronic fatigue, and depression.

Fourth, thiamin in the yeast extract composition is involved in the nervous system, for example, for normal heart and nerve tissue activities. Low blood thiamin content results in depression, emotional instability, somnipathy, irritability, hyperaction, etc. However, these symptoms are known to disappear by the administration of thiamin (Professor Rus Harrel, Colombia University in New York). Therefore, PMS in women, such as depression, emotional instability, somnipathy, and irritability, can be treated with the thiamin-rich yeast extract.

Fifth, riboflavin in the yeast extraction composition is involved in the synthesis of coenzymes, FMN (flavin mononucleotide) and FAD (flavin adenine dinucleotide). These coenzymes help oxidize nutrients for energy production and synthesize red blood cells and adrenocortical hormone. Accordingly, riboflavin is essential in the period of menstrual bleeding.

Sixth, the mineral selenium in the yeast extract has an antioxidant effect about 1,900 times greater than vitamin E. Neurotransmitters, including serotonin, synthesized in the body may lose their activity by oxidation in the gastrointestical tract or during transmission. Here, the antioxidant selenium aids the neurotransmitters, such as serotonin, to maximize their effects by preventing oxidation of the neurotransmitters.

Finally, an excess of minerals such as calcium and magnesium are required to relieve menstrual pains. Minerals are rapidly absorbed into the body when taken as a food, and their absorption rate is increased with the supply of amino acids. Since the yeast extract are rich in both minerals and amino acids, the minerals can be easily absorbed into the body to effectively manage PMS and menstrual pains. Through the mechanism as described above, the yeast extract can effectively alleviate PMS and menstrual pains.

In another aspect of the present invention, there is provided a PMS and menstrual pain relaxant composition further including chitosan in addition to the yeast extract.

Chitosan is known as an active material to enhance autoimmune response, to aid in the absorption of calcium, and to regulate cholesterol levels. Calcium is an essential mineral for women, especially in the period of menstrual bleeding to relieve PMS. Chitosan is highly effective in removing foreign substances as well as helps calcium absorption, and thus it is useful in relieving PMS and menstrual pains. According to the present invention, it is preferable to use a water-soluble polymeric chitosan of a molecular weight greater than or equal to about 300,000.

Alternatively, the PMS and menstrual pain relaxant composition according to the present invention may further include a herb, such as Korean angelica root, Salviae Radix, *Curcuma aromatica*, Zedoariae Rhizoma, mint, liquorice, ginger, *Gastrodia*, white *Atractylis, Cnidium officinale*, cinnamon, and ginseng.

The above-listed herbs, such as Korean angelica root, Salviae Radix, *Curcuma aromatica*, liquorice, mint, ginseng, cinnamon, and ginger, are known to aid in the circulation of blood, the dispersal of extravasated blood, the alleviation of pain, the increase of appetite, the activation of metabolism, especially for woman (refer to a text of herbalogy). Congestion due to the non-smooth circulation of blood during the menstrual cycle may cause menstrual pains. The above-listed herbs can alleviate the menstrual pains.

*Gastrodia, cnidium officinale*, white *Atractylis*, Zedoariae Rhizoma, etc. aids in the brain blood circulation and in the generation of neurotransmitters to clear head.

Each of the components of the PMD and menstrual pain relaxant composition is ground and mixed with the composition of about 10-90% by weight yeast extract, about 50-80% by weight chitosan, and about 5-80% by weight the herb, based on the total weight of the composition. If excess yeast extract is added, a feeling of langor may result for a patient with mild pain, but an effective reduction in pain results for a patient with severe pain. Therefore, it is preferable to adjust the amount of yeast extract added within the above range.

If excess chitosan is added, the acidity of chitosan itself may act as a stimulus in the body to cause excess tension or stress in a patient with severe menstrual pains, but no adverse effect on a normal person.

The lower limits of the yeast extract and chitosan added are determined to be at least about 10% by weight and about 5% by weight, respectively, to appropriately induce the relaxation effect of the yeast extract and the stimulation effect of the chitosan for effective metabolism in the body. The upper limits of the yeast extract and chitosan added are determined to be about 90% by weight and about 80% by weight, respectively, to appropriately induce the relaxation effect of the yeast extract and the stimulation effect of the chitosan for effective metabolism in the body.

The lower limit of the herb is determined to be at least about 5% by weight by considering its effect of dispersing the extravasated blood remaining after the menstrual cycle. An effective PMS and menstrual pain relaxant composition according to the present invention can be prepared with the addition of at least about 5% by weight the herb.

A method for preparing the yeast extract according to the present invention will be described in greater detail.

In the preparation of the yeast extract according to the present invention, yeast is additionally subjected to a stress, such as high-temperature heating, ultrasonic waves, and vibrations, to secrete stress-resistant substances. This additional step performed at a temperature higher than a lethal temperature of the yeast induces autolysis to utilize active components of the yeast biomass. Here, the yeast's ability to selectively permeate the cell wall is lost, and the cell wall is destroyed by enzymes existing in the yeast, such as protease, lipase, invertase, maltase, zymase, etc. Through the autolysis, a variety of taste components, including amino acids, such as glutamic acid, and nucleic acid metabolites, such as 5'-AMP, are released (Hyung-ik Song and Jung-yeub Shin, Contemporary Fermentation Engineering, 1998, 5:189). Simultaneously, pappain as a protease is added to efficiently give activities as an anti-stress agent, an anti-fatigue agent, and a neurotrophic factor.

Temperature is one of important factors affecting the growth and survival of yeast. Most microorganisms are mesophilic. Yeast has a limited growth temperature of 20-46° C. *Saccharomyces cerevisiae*, mesophilic yeast, is subjected to a mild thermal shock at 37° C. to induce cell resistance to a lethal temperature of 48-55° C. The resulting thermally resistant cells produce the diose trehalose and effective thermal shock proteins of 90 kDa, 70 kDa, and 60 kDa even with a rise of only 5° C. in temperature from their optimal growth temperature of 35° C. (Michell L. Deegenaars and Kenneth Watson, Environmental Microbiology, the edition of August, 1998). This report supports the fact that yeast produces anti-stress proteins when subjected to thermal stress. Based on this fact, the inventor has additionally induced the synthesis of anti-stress substances by heating at high-temperature and by applying ultrasonic waves and vibrations in the preparations of the yeast extract and yeast-derived peptide according to the present invention. In addition, the method for preparing the yeast extract and yeast-derived peptide according to the present invention involves hydrolying the yeast protein with an addition of a protease while autolysing the yeast at a high-temperature of 35-70° C., and centrifuging the hydrolytes to separate a supernatant.

To investigate the anti-stress capability of the yeast extract and yeast-derived peptide according to the present invention as a neurotrophic factor, an immobile stress test was performed based on the Brekhman and Dardymov method. In general, a series of bioreactions occurring due to stress are initiated by the central nervous system's detection of an external stimulus. Adrenocortical hormone secretion is affected according to the external stimulus to cause changes in the weight of liver, thymus, thyroid gland, and spleen and a reduction in the number of immunocytes. Also, lactate dehydrogenase (LDH) and alkaline phosphatate (ALP) levels in blood are known to change due to an effect of corticosteroid. Changes the above-listed indices have been applied to evaluate anti-stress capability (Cristina, J., Hans, W. and Hans, M., Haematological changes during acute mental stress, Bri. J. Heanat 71:564, 1971; Conner, R. L., Vernikos-Danelis, J. and Levine, S., Stress, fighting and neuroendocrine function, Nature, 2:564, 1971; Munck, A., Guyre, P. M. and Holbrook, N. J., Physiological functions of gluococorticoids in stress and their relation to pharmacological actions, Endocrine Review, 6:25, 1984). As a result of the immobile stress test with rats based on the above anti-stress indices, where changes in the weight of organs and in the level of hemato-biochemical factors were measured, the yeast extract and yeast-derived peptide according to the present invention was verified to have the anti-stress effect.

A swimming endurance test was performed to measure the anti-fatigue capability, a kind of anti-stress test, of the yeast extract and yeast-derived peptide according to the present invention. In general, stress is known to affect bipolar affective reaction, motional function, and autonomous function (Yei-wan Hwang, Psychosomatosis, pp. 17-28, 33-49, and 272, Haenglim Publishing Co., Seoul, Korea). Excess exercise, such as swimming, is considered as a stress. Therefore, the swimming endurance test performed using an experimental swimming pool, where excess swimming was forced to measure the powder of endurance, to determine an anti-fatigue effect is considered to be suitable for measuring an anti-stress effect. As a result of the test, the yeast extract and yeast-derived peptide according to the present invention was proven to have excellent anti-stress and anti-fatigue effects.

As another test to measure the anti-stress effect of the yeast extract and yeast-derived peptide according to the present invention, the effect of regulating the autonomic nervous system was determined with patients with anxiety. 200 g of the yeast hydrolyte was orally administered three times a day for 1 week, and the effect of regulating the autonomic nervous system was measured using a stress measurement device (SA-2000, Medicore, Korea). The cardiac cycle (heart rate variability) obtained through power spectral density (PDS) analysis was analyzed for each 5-minute segment to obtain a 5-minute total power. As a result of the autonomic nerve regulation test with the administration of the yeast extract of the invention, autonomic nerve regulation and the ability to regulate against stress- and pain-inducing substances were enhanced with the expectation of its effect on painful PMS similar to stress symptoms.

To verify the bioactivity of the mineral-enriched yeast extract according to the present invention greater than other peptide substances, a macrophage activity test was performed on the mineral-enriched yeast extract to measure immunity. Macrophages, immunocytes involved in both congenital and adaptive immune systems, are critical in the cell-mediated immunity (CMI) to provide antigens for inducing lymphocytes through digestion and successive decomposition and other processes of externally introduced substances, to secrete specific substances, such as immunoregulatory cytokine, and to produce nitric oxide (NO) having the function of killing foreign invaders, antigens. Macrophages are divided into inflammatory macrophages and activated macrophages depending on activity. Inflammatory macrophages are produced when exposed to inflammation inducer substances, such as thioglycolate. The inflammatory macrophages have phagocytic activity and surface adherence, and increase the secretion of prostaglandin, the ability to synthesize protein of a variety of enzymes, such as plasminogen activating enzyme, elastase, collagenase, etc., cell size, and the release of a number of cellular discharges.

Macrophages activated by cytokines, such as IFN-γ and TNF, and lipopolysaccaride (LPS) from gram-negative microorganisms have anti-cancer and anti-microbial effects. In the cytotoxic mechanism of the macrophages with respect to cancer, cytokines, such as TNF-α, IL-1, IL-6, IL-8, and IL-12, hydrogen peroxide ($H_2O_2$), nitric acid (NO), and cytolytic protease which are released from the activated macrophages are known to have a toxicity with respect to cancer cells. The macrophages activated by such lectins, large molecular proteoglycan, and polysaccharide primarily suppress oncogenesis and then tumor metastasis, and have the ability to distinguish oncocytes and normal cells. Although a target structure the macrophage can detect has not been identified yet, unlike the phagocytosis mechanism of the macrophage, the macrophage adheres to a target oncocyte to release lysosomal enzymes before lysis of the target oncocyte. Meanwhile, non-activated macrophages have a weak toxicity to tumor cells and thus needs to be activated for enhanced oncolytic abilities. This fact supports that immunotherapy to lead macrophage activation can be an effective therapy. Accordingly, the microphage activity was tested for the mineral-enriched yeast extract according to the present invention. As a result, it was proven that the mineral-enriched yeast extract according to the present invention is effective in enhancing immunity.

The bioactivity of the mineral-enriched yeast extract according to the present invention greater than other peptide substances was additionally verified through an intestinal immunity activity test to measure immunity. Immunocytes constitute tissues or organs, called the lymphatic system, for effective immune reactions. The lymphatic system is classified into primary (or central) lymphoid organs, including bone marrow and thymus, for producing lymphocytes, and secondary lymphoid organs, including lymph nodes, spleen, and mucosa-associated lymphoid tissues (MALT), for providing conditions or environments for the contact of the lymphocytes and antigens and the interactions between lymphocytes. The MALT, which is located at a region susceptible to microorganisms, plays an important role in regional, mucosal immune reactions, so it is called the mucosal immune system. The MALT, which induces a defective reaction against antigens entering the body via ingestion or inspiration, is classified into the gut-associated lymphoid tissues (GALT) located in digestive track, the bronchous-associated lymphoid tissues (BALT) located in the musculi canal, and the nasal-associated lymphoid tissues (NALT) located in the junction of the plate and nose. Among these types of lymphoid tissues, the GALT as the largest lymphoid tissue present in the intestinal mucosa is especially significant in the body protective system. The alimentary mucosa having a large surface area is always exposed to a number of different microorganisms and plant-derived heterologous proteins or compounds, which supports the immunological significance of the GALT.

Peyer's patches used in the examples according to the present invention to be described later, which have the typical structure of the GALT, are an aggregate of nodi lymphatici mesenterici distributed in the small intestinal mucosa. Peyer's patches are easily observed, and most are observed in the ileum. Activated lymphocytes in the Peyer's patch release a variety of cytokines, including IL-6 and GM-CSF (granulocyte macrophage-colony stimulating factor), to regulate immune or inflammatory reactions by regulating the growth, migration, proliferation of bone marrow cells, white blood cells, and hematogenic cells. Based on this fact, in an example according to the present invention to be described later the degree of proliferation of bone marrow cells by cytokines secreted with the activation of the Peyer's patch cells using the mineral-enriched yeast extract according to the present invention was measured to determine enhanced immunoactivity.

In general, a stimulus to the human body is known to be injurious if it's intensity is over the limit, thereby causing tension headaches, migraine headaches, hypertension, indigestion, fatigue, or generalized headaches. If such a stimulus is prolonged chronically, non-specific general adaptative syndromes, such as neuropathies or gastropathies, may result (Yei-wan Hwang, Psychosomatosis, pp. 17-28, 33-49, and 272, Haenglim Publishing Co., Seoul). As described above, the yeast extract and yeast-derived peptide according to the present invention have an anti-stress effect and can be used as a tranquilizer or a relaxtant. In particular, it is greatly expected to use the yeast extract and yeast-derived peptide according to the present invention as a sleeping aid for nervous people with sleeping problems. The yeast extract and yeast-derived peptide according to the present invention are useful as a source for auxiliary health foods and special nutritional foods having an activity as a brain-neurotrophic factor for relieving the above symptoms.

As described above, the yeast extract and yeast-derived peptide according to the present invention are effective in the regulation of the autonomic nervous system, for example, in alleviating stress and inducing deep sleep. The yeast extract and yeast-derived peptide according to the present invention are believed to be an effective neurotrophin for normalizing the neurological function without any side effect for excess doses.

Unlike conventional side-effect inducing therapeutic drugs for nervous and stress symptoms, such as a tranquilizer, an anti-anxiety agent, a sleeping drug, etc., the yeast extract and yeast-derived peptide according to the present invention prepared from a natural source and having anti-stress and neurotrophic effects can effectively regulate the autonomic nervous system to alleviate a number of stress symptoms without any side effect. In particular, the yeast extract and yeast-derived peptide according to the present invention are applicable as a tranquilizer, an anti-stress agent, a sleeping aid, an anti-fatigue agent, and PMS and menstrual pain relaxants.

The yeast extract and yeast-derived peptide according to the present invention having the anti-stress and neurotrophic effects are available as a substitute for conventional side-effect inducing psychotrophic drugs in the preparation of medicines, active foods, medicines and feed for animals, etc. For use of the yeast extract and yeast-derived peptide according to the present invention as therapeutic agents, a variety of known pharmaceutical methods can be applied in the preparation of those drugs. The yeast extract and yeast-derive peptide according to the present invention may be processed alone or mixed with a pharmaceutically safe carrier, vehicle, diluent, etc. into powder, granule, tablet, capsule, or injection form to be orally or non-orally administered.

When the yeast extract and yeast-derived peptide according to the present invention are used as a therapeutic agent, its dose can be appropriately determined depending on the age, sex, state, and symptom of a patient. Preferably, the yeast extract or yeast-derived peptide according to the present invention is used at a dose of about 10-500 mg a day for adults. For a patient with insomnia, a capsule containing 250 mg of the yeast extract or yeast-derived peptide powder is administered twice a day.

For use of the yeast extract according to the present invention as a PMS and menstrual pain relaxant, the yeast extract is ground, and capsules are filled with the yeast extract powder. Alternatively, the yeast extract powder may be processed into tablets. When a dose of 1-2 capsules (or tablets) two or three times a day, each capsule (or tablet) containing 180 mg of the yeast extract powder, is taken with excess water, PMS, menstrual pains, hysterorrhea, and dysmenorrhea in females are effectively alleviated.

The yeast extract and yeast-derived peptide according to the present invention or a composition containing the same are applicable in the preparation of heath beverages effective in relieving females of PMS, menstrual pains, hysterorrhea, etc.

EXAMPLES

The present invention now will be described more full with reference to the accompanying drawings, in which preferred examples of the invention are shown. This invention may, however, be embodied in different forms and should not be constructed as being limited to the examples set fourth herein; rather, these examples are provided so that this disclosure will be thorough and complete, and will fully convey the concept of the invention to those skilled in the art.

Example 1

Preparation of Yeast Extract

Yeast (*Saccharomyces cerevisiae* IFO 2346) was cultured in media containing 2% glucose, 0.6% (NH4)2SO4, 0.1% MgSO4.7H2O, 0.2% KH2PO4, 0.03% K2HPO4 and 0.1% NaCl. The resulting cultures were centrifuged at 3,000×g to recover the yeast. The recovered yeast was added with 50× volume of phosphate buffer and 0.5% of protease (papain) and hydrolyzed at 30° C. for 6 hours.

The hydrolytes were placed in 100° C. water bath to inactivate the protease and centrifuged at 8,000×g to separate the supernatant. The supernatant was freeze-dried and the resulting yeast extract was referred to as SCE (*Saccharomyces cerevisiae* extract). SCE was separated into above 10,000 Da MW fraction (Above 10 k) and below 10,000 Da MW fraction (Below 10 k) by centrifuging at 3,000×g.

Example 2

Preparation of Yeast Extract

*Saccaromyces* cerevisiae (raw yeast purchased from Jenico Co.), food-grade yeast strain, was cultured in a YM medium at 24° C. for 48 hours with the supply of oxygen.

The resulting cultures were centrifuged at 15,000 rpm for 15 minutes to remove a supernatant. The remaining yeast precipitate was washed twice and diluted with 10-fold (v/v) sterile water. The yeast was autolyzed at a high temperature of 50° C. by an autolytic enzyme which the yeast inherently has, and simultaneously yeast protein was hydrolyzed into peptides at a initial pH of 4.0 for 48 hours with an addition of 1% protease (papain 30,000) for accelerating the hydrolysis.

The resulting hydrolytes were centrifuged at 15,000 rpm to separate a supernatant as a yeast extract according to the present invention. The yeast extract was freeze-dried and labeled with "Sample 1" to be used in the following examples.

Example 3

Preparation of Yeast Extract

1) Screening of Enhanced Yeast Strain.

*Saccaromyces* cerevisiae strain 7904, recognized as food-grade and obtained from the Korean Collection for Type Culture (KCTC), was incubated for 48 hours under stress from continuous 45 kHz-ultrasonic waves and vibrations resulting from a waterfall generated by a water-pump, to screen a surviving yeast strain resistant again the stress. The surviving yeast strain was plated on YM agar plate (containing 3 g/L yeast extract, 3 g/L malt extract, 5 g/L peptone, 10 g/L glucose, and 15 g/L agar) to screen an enhanced yeast strain forming a largest colony at a highest growth rate.

2) Incubation

The screened enhanced yeast strain was placed on YM medium and incubated in a fermentor supplied with oxygen, at 24° C., for 48 hours. The resulting cultures were centrifuged at 15,000 rpm for 15 minutes to remove a supernatant.

The remaining yeast paste precipitate was diluted with 10-fold (v/v) 1% peptone buffer. In a fermentor equipped with an ultrasonic wave generator and a vibrator, the yeast paste was subjected to stress from heating at a high temperature of 35-45° C. and 45 kHz-ultrasonic waves for 30 seconds. This application of the stress was repeated at a 5-min interval for a total of 8 hours while another stress of vibrations from a waterfall generated by a water-pump was applied to the yeast paste, to secrete excess anti-stress substances.

3) Autolysis and Hydrolysis

The cultures from the incubation process was autolyzed at a high temperature of 50° C. by an autolytic enzyme which the yeast inherently has, and simultaneously yeast protein was hydrolyzed into peptides at a pH of 4.0 for 48 hours with an addition of 1% protease (papain 30,000) for accelerating the hydrolysis.

After the hydrolysis, the degree of hydrolysis was calculated by dividing a protein concentration of the supernatant by a total protein concentration of the yeast. To determine the protein concentration, the autolyzed yeast paste was centrifuged to recover a supernatant. After dilution of the supernatant, 500 μL of the dilute was pipetted into a tube and mixed with the same portion of a protein-quantitative reagent. The mixture was reacted at 60° C. for 60 minutes with stirring and measured at 562 nm using a spectrophotometer. As a result, the degree of hydrolysis was 55%.

4) Separation, Purification, and Drying of Hydrolytes

The resulting hydrolytes from the autolysis and hydrolysis was centrifuged at 15,000 rpm to recover an aqueous supernatant. The recovered supernatant was labeled "Sample 2", whereas the precipitate from the centrifugation was labeled "Sample 3" to be used in the following examples. The supernatant and the precipitate were freeze-dried and ground to produce yeast extract powder and precipitate powder, respectively.

5) Ultrafiltration

The supernatant was subjected to separation and purification using a ultrafiltration membrane having a molecular weight cutoff (MWCO) value of 10,000, followed by freeze-drying, to produce natural yeast-derived peptides having a molecular weight smaller than or equal to 10,000.

Example 4

Composition Analysis

The general components of the yeast hydrolytes prepared in Example 2 were analyzed by AOAC methods: moisture content by an air oven drying method at 105° C., crude protein by a microKjeldahl method, crude lipid by Soxhlet extraction, and crude ash by ashing at 550° C.

The results are shown in Table 1. As shown in Table 1, protein content was highest as 60.1%, and carbohydrate was comparatively high as 26.9%. Comparing to general yeast extract containing 45-60% protein and 35-45% carbohydrates, the yeast hydrolytes according to the present invention was slightly higher in protein content and slightly lower in carbohydrate content than the general yeast extract.

TABLE 1

| Analyzed Item | Method | Feature of Yeast Extract (Present Invention) |
|---|---|---|
| Appearance | Sensory test | Yellowish brown powder |
| Moisture | Air Oven Dry Method | 4.7% (max. 7%) |
| Crude lipid | Soxhlet Extraction Method | 0.3% (max. 7%) |

TABLE 1-continued

| Analyzed Item | Method | Feature of Yeast Extract (Present Invention) |
|---|---|---|
| Crude protein | Semi-micro-Kejeldahl method (nitrogen coefficient = 6.25) | 60.1% (min. 30%) |
| Carbohydrate | — | 26.9% (max. 30%) |
| Sodium | I.C.P. method | 721.2 (mg/100 g, max. 750) |
| Vitamin B1 | — | 26.12 (mg/100 g, min. 20) |
| Vitamin B2 | — | 20.13 (mg/100 g, min. 15) |
| Vitamin B6 | — | 10.61 (mg/100 g, min. 5) |
| Vitamin B12 | — | 135.8 (mg/100 g, min. 100) |
| E. coli. | — | Negative |
| UV stability | 12-hour irradiation (30% yeast extract solution) | Mild yellow (no change in color) |
| Acid resistance | 0.67% (equivalent to citric acid) (30% SCP-20 solution) | No precipitate (after 12-hour left at room temperature) |
| Thermal resistance | heating in 100° C. water for 30 min (30% SCP-20 solution) | No significant change in color |

Amino acid contents in protein were analyzed by the following method. 10 g of the yeast extract obtained from Example 2 was dehydrated with cooling acetone and dried on a filter paper in a dry oven at 60° C. 5 mg of the dried sample was placed into a hard test tube and degassed with an addition of 5 mL of 6N HCl, followed by tight sealing. After hydrolysis at 110° C. for 24 hours, hydrolytes were washed with a small amount of distilled water 2-3 times and concentrated and dried at 50° C. by an evaporator to remove the HCl. The resulting concentrate was dissolved in a buffer and eluted into an amino acid analyzer (Deckman System 6300, USA) equipped with a 10 cm-ion exchange column (No. 338051). The amino acid composition of the yeast extract according to the present invention as the result of the analysis is shown in Table 2.

TABLE 2

| Amino Acid | Mol % |
|---|---|
| Glutamic acid | 14.2 |
| Leucine | 6.9 |
| Lysine | 5.2 |
| Aspartic acid | 5.0 |
| Alanine | 4.7 |
| Histidine | 4.3 |
| Isoleucine | 3.9 |
| Phenylalanine | 3.7 |
| Valine | 3.4 |
| Tyrosine | 3.5 |
| Threonine | 3.0 |
| Glycine | 3.0 |
| Serine | 2.8 |
| Arginine | 2.3 |
| Proline | 2.0 |
| Tryptophan | 1.4 |
| Methionine | 1.5 |
| Cysteine | 0.8 |

As shown in Table 2, the yeast-derived peptide prepared according to the present invention contained 18 kinds of different amino acids with high aspartic acid and glutamic acid contents. As is apparent from the result of the amino acid analysis, the variety of amino acids and peptides can act as anti-stress neurotrophic factors for regulating imbalance in the autonomic nervous system caused under excess stress.

Example 5

Preparation of Pharmaceutical Composition (Capsule)

The freeze-dried powder of the supernatant (Sample 2) prepared in Example 3 was used. Korean angelica root, Salviae Radix, *Curcuma aromatics*, Zedoariae Rhizoma, mint, liquorice, and ginseng were ground and mixed in the same weight ratio to prepare a herbal mixture. Water-soluble polymeric chitosan (from Jakwang Chitosan Co.) of a molecular weight greater than 300,000 daltons was purchased.

The yeast extract, the chitosan, and the herbal mixture were mixed in a weight ratio of 40:30:30, and each capsule was filled with 180 mg of the mixture.

Example 6

Preparation of Function Food (Beverage)

1) Filtration and Purification

The supernatant from Example 3 was mixed with active carbon (5% by weight of the supernatant), and stirred with about 20-fold water. The mixture was sterilized in a pressure sterilizer at 121° C. for 15 minutes, followed twice by filtration with suction to produce a decolorized, deodorized, purified yeast extract.

2) Preparation of Beverage Composition

The yeast extract prepared through the filtration and purification was diluted with 70 weight part of water. 7% by weight liquid fructose, 4% by weight glucose, 5.9% by weight ume juice concentrate were added into the dilute to prepare a beverage composition.

3) Effect of Additives

To compensate for the inherent poor preference of the source material yeast, a sweetener and an acidulant were added in the preparation of an anti-stress beverage with the yeast extract. Sensory evaluation was performed by a 5-scale test to determine the effect of elevating the preference and an optimal mixing ratio. On the 5-scale test, each sensory characteristic was evaluated using five levels, including end and middle levels, extremely dislike (score 1), moderate (score 3), extremely like (score 5). The result of the sensory evaluation is shown in Table 3.

TABLE 3

|  | Additive | Color | Flavor | Taste | Overall Preference | Remarks |
|---|---|---|---|---|---|---|
| Sweetener | 3% Liquid fructose | 4.2 | 3.8 | 2.5 | 3.5 | 5% Ume juice concentrate added |
|  | 5% Liquid fructose | 4.2 | 3.9 | 3.0 | 3.7 |  |
|  | 7% Liquid fructose | 4.4 | 4.1 | 3.5 | 4.0 |  |
|  | 9% Liquid fructose | 4.2 | 4.1 | 3.5 | 3.9 |  |
|  | 2% Glucose | 4.0 | 3.9 | 2.5 | 3.5 |  |
|  | 4% Glucose | 4.0 | 3.9 | 3.5 | 3.8 |  |
|  | 6% Glucose | 4.0 | 3.9 | 3.2 | 3.7 |  |
| Acidulant | 4% Ume juice concentrate | 3.5 | 3.4 | 3.9 | 3.6 | 8% Liquid fructose added |
|  | 6% Ume juice | 4.0 | 4.0 | 4.3 | 4.1 |  |
|  | 8% Ume juice concentrate | 4.1 | 4.2 | 4.0 | 4.1 |  |

TABLE 3-continued

The effect of additive was investigated with different kinds of additives at different mixing ratios. As shown in Table 3, the overall preference was best when 7% liquid fructose was added together with 5% ume juice concentrate which was previously determined to be optimal. When glucose was added as a sweetener, the overall preference was best at 4%. There was no difference in preference for color and flavor between different glucose levels, but there was for taste. When the ume juice concentrate was added in different amounts together with 8% liquid fructose, the overall preference was the same, between 6% and 8%, but flavor preference was greatly different between the two levels. In other words, the addition of liquid fructose or glucose was effective in the improvement of preference for taste, and the addition of ume juice concentrate provided a cool feeling by enhancing the flavor and a sour taste. Based on the results of the sensory evaluation, proper amounts of liquid fructose and glucose added as a sweetener were determined to be about 7% and 4%, respectively, and an proper amount of ume juice concentrate added as an acidulant was determined to be in the range of about 6-8%.

Example 7

Preparation of Functional Food (Chewing Gum)

The SCE prepared in Example 1 was used. 40% by weight sugar powder, 17% by weight anhydrous glucose, 10% by weight grinded xylitol, 0.1% by weight citric acid, 0.02% by weight aspartame and 1% by weight SCE were dissolved and added with 30% by weight chewing base (Chewing Gum Base K-0121, Borac, Korea). After that, 1.88% by weight apple powder (Apple ST-1003, Takada, Japan) was added, heated with mixing for 30 minutes, and rolled to produce a chewing gum.

Example 8

Preparation of Functional Food (Edible Film)

The SCE prepared in Example 1 was used. Mixture of 3% by weight glycerol, 90% by weight water was suspended with 6% by weight pulluran and 1% by weight SCE. The suspension was heated to 85° C. and dissolved with stirring for 60 minutes. The obtained solution was maintained at 85° C., degassed under reduced pressure and transferred onto a drum heated by cycling with 95° C. hot bath to cast a film continuously. After placed on the drum for 4 minutes, the obtained film was taken out and cut in the size of 3 cm×2 cm to prepare an edible film.

Experimental Examples

The yeast extract according to the present invention was tested in the following examples for its activities as a selective serotonin and norepinephrine reuptake inhibitor, an anti-depression agent, anti-anxiety agent, an anti-stress agent, an anti-fatigue agent, an anti-obesity agent, an autonomic nerve regulator, and a PMS and menstrual pain relaxant.

Experimental Example 1

Affinity Test to Serotonin Transporter (SERT) and Norepinephrine Transporter (NET)

To assay the yeast extract's affinity to serotonin transporter (SERT), [3H]paroxetine binding experiment was carried out. [3H]paroxetine is a agent which can inhibit uptake of serotonin by selectively binding to pre-synaptic serotonin transpoter/reuptake region (Dewer et al., 1992). From male white rats (Sprague-Dawley rat, 280-350 g), cerebral cortex was isolated, put in 10x volume of cold buffer (50 mM Tris, 120 mM NaCl, 5 mM KCl, pH 7.4), homogenized using Brinkmann polytron grinder, and centrifuged at 4° C., 48,000×g for 10 minutes. After adding 10× volume of the same cold buffer to the precipitate, centrifugation was repeated 3 times under the same condition. The measurement was carried out repeatedly in three test tubes. The total amount was 0.5 ml. Each test tube was added with competing agents (SCE, Above 10 k, Below 10 k) 50 µl, buffer 100, and cortex cell membrane sample 250 µl (100 µg protein/tube), was pre-cultured at 25° C. for 10 minutes, added by 1 nM [3H]paroxetine 100 µl, and cultured at 25° C. for 1 hour. To the test tubes for measuring total binding amount and non-specific binding amount, buffer and 10 µM paroxetine were added instead of the competing agents respectively. After the culturing was finished, it was rapidly filtrated using a cell harvester via GF/C filter (Whatman, England) pre-immersed in 0.05% polyethyleneimine to finish the reaction. The filter was washed 3 times with 4 ml of cold buffer and transferred to a liquid scintillation vial. The vial was added with 2 ml of counting cocktail after wetted with 0.5 ml of EtOH. From the filter, remaining radio-activity was measured using liquid scintillation counter (Packard, Tr-3500). Protein quantification was carried out according to Lowry et al's method (1951).

To assay the yeast extract's affinity to norepinephrine transporter (NET), [3H]nisoxetine binding experiment was carried out. [3H]nisoxetine is a selective inhibitor of norepinephrine transporter which have been used for confirming the mechanism of an antidepressant. The experimental procedure was the same as that of serotonin transporter expect that 0.7 nM [3H]nisoxetine was used instead of [3H]paroxetine and 10 µM desipramine was used for nonspecific binding. Competing agents (SCE, Above 10 k, Below 10 k), buffer and cortex cell membrane sample were added to the test tube, pre-cultured at 4° C. for 20 minutes, added by 0.7 nM [3H] nisoxetine, and cultured at 4° C. for 3 hour. The total amount was 250 µl.

SERT and NET are related to many psychiatric diseases such as depression and anxiety (Frazer et al., 1999; Masson et al., 1999). Na+/Cl-- dependant serotonin transporter was known as acing point of psychiatric drugs such as antidepressant and meth-amphetamine (Douglas and Munro, 1982; Rowland and Carlton, 1986; Rundnick and Wall, 1991). Certain changes of serotonin transporter are related to depression, anxiety and autism (Cook et al., 1997; Lesch et al., 1994; Oglivie et al., 1996). Serotonin transporter is inhibited by antidepressant such as fluoxetine and paroxetine (Barker et al., 1994). Tricyclic antidepressant, for example desipramine, is a selective NE reuptake inhibitor (Kientsch et al., 2001).

Figure 3:
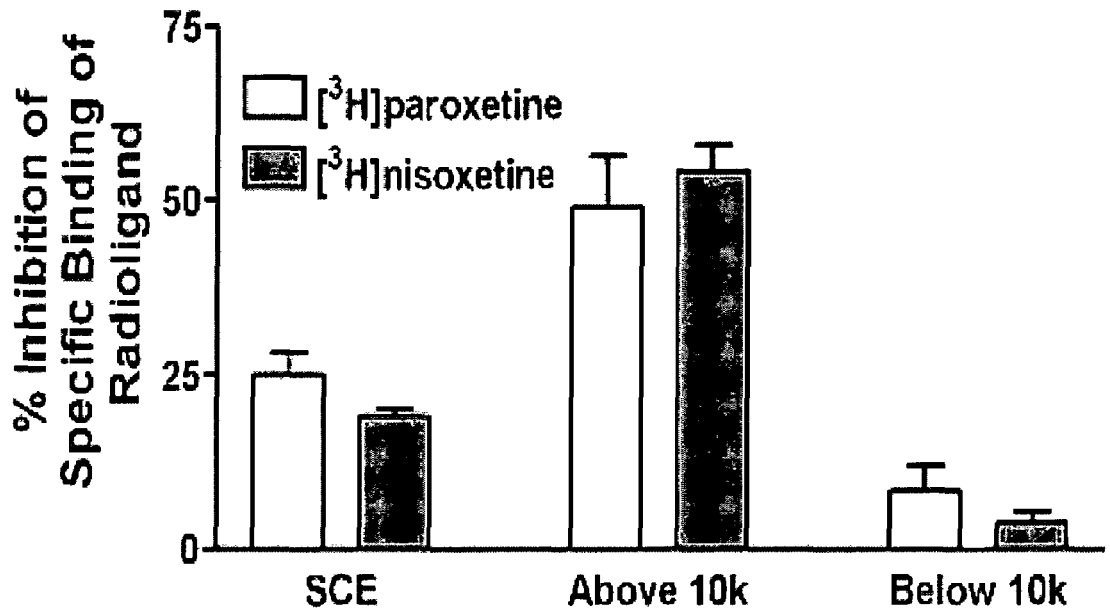
FIG. 3 is a graph showing the inhibiting effects of the present yeast extract on the specific binding of [3H]paroxetine and [3H]nisoxetine in white rat's cerebral cortex membranes.

Therefore, in order to confirm the anti-depression and anti-anxiety effects of the present invention, the present yeast extract (referred as 'SCE')'s affinity to SERT and NET was tested. SCE (1 mg/ml) inhibited binding of [3H]paroxetine and [3H]nisoxetine about 25% in white rate's cerebral cortex cell membrane sample. A fraction with above 10 k MW (referred as 'Above 10 k') showed more than 50% of inhibition effect, whereas a fraction with below 10 k MW (referred as 'Below 10 k') showed about 10% of inhibition effect at the same dose (FIG. 3). FIG. 3 is a graph showing the inhibiting effects of the present yeast extract on the specific binding of [3H]paroxetine and [3H]nisoxetine in white rat's cerebral cortex membranes. In the FIG. 3, data is expressed as mean ±SEM, SCE means whole yeast extract, Above-10 k means a fraction with above 10000 Da, Below-10 k means a fraction with below 10000 Da. As seen in FIG. 3, SCE and Below 10K show selective binding-inhibition effects, especially Above 10K shows more than 50% of inhibition effects to both of [3H]paroxetine and [3H]nisoxetine.

Experimental Example 2

Serotonin Binding Assay

An activity of the present yeast extract to inhibit binding of human serotonin transporter and Paroxetin $H^3$ was measured with radioactivity. Firstly, human serotonin receptor protein, Paroxetin $H^3$ and the present yeast extract (SCE) were mixed according to concentrations, reacted at 30° C. for 30 minutes, after stopping the reaction washed 10 times with a GFC filter. After drying well, a scintillation solution was added and CPM (counts per. minute) was measured. As a standard compound, Prozac was used. The resulting data are as follows.

TABLE 4

Paroxetin's binding degree according to concentrations

| Concentrations | CPM |
|---|---|
| 0 nM of Paroxetin | 128 |
| 0.1 nM | 455 |
| 1 nM | 3100 |
| 10 nM | 5950 |

TABLE 5

Inhibition degree of the present yeast

| Concentrations | % Inhibition |
|---|---|
| 1000 nM of Prozac | 99 |
| 1 mg of SCE | 15 |
| 4 mg of SCE | 21 |
| 10 mg of SCE | 34 |
| 20 mg of SCE | 77 |

Experimental Example 3

Test on Reuptake of Serotonin
(5-hydroxytryptamine: 5-HT) and Norepinephrine
(NE)

To confirm whether the present yeast extract can inhibit reuptake of serotonin (5-HT), [3H]5-HT uptake experiment was carried out. From male white rats (Sprague-Dawley rat, 280-350 g), cerebral cortex was obtained, grinded using Teflon glass grinder, centrifuged at 4° C., 1,000×g for 10 minutes. Supernatant was pooled apart, precipitate was added again with 10× volume of the same buffer, and centrifuged under the same condition. The precipitate was removed, both of supernatants were pooled, and centrifuged at 4° C., 20,000×g for 20 minutes. The resulting supernatant was removed and a synaptosome layer was separated from below mitochondria layer using 200 µl of uptake buffer (127 mM NaCl, 5 mM KCl, 1.3 mM NaH2PO4, 1.2 mM MgSO4, 2.5 mM CaCl2, 15 mM HEPES acid, 10 mM glucose, pH 7.4) with several weak shakings. Protein concentration of synaptosome was 2 mg protein/ml. Before the uptake measurement, competing agents (SCE, Above 10 k, Below 10 k) 50 µl, buffer 250 µl and synaptosome sample 100 µl (0.2 mg protein) were added, pre-cultured at 37° C. for 10 minutes, added by 15 nM [3H]5-HT 100 µl, and cultured at 37° C. for 5 minutes. In the test tube for nonspecific reaction, 10 µM fluoxetine was used. To prevent uptake of [3H]5-HT to dopamine and norepinephrine terminuses, 1 µM nomifensine and 0.1 µM nisoxetine were added. Uptake culture was terminated by adding 2 ml of cold buffer to each test tube, and then rapidly filtrated using a cell harvester via GF/C filter (Whatman, England) pre-immersed in 0.1% polyethyleneimine. The filter was washed 3 times with 2 ml of cold buffer, transferred in scintillation vial and measured.

To confirm whether the present yeast extract can inhibit reuptake of norepinephrine (NE), [3H]NE uptake experiment was carried out. The experimental procedure was the same as that of serotonin expect that 1 nM [3H]NE was used instead of [3H]5-HT and 10 µM desipramine was used for nonspecific binding. Synaptosome was 3.5 mg protein/ml. For [3H]DA uptake experiment, 0.5 nM [3H]DA was used instead of [3H]5-HT and 1 µM nomifensine was used for nonspecific binding. Synaptosome was 2 mg protein/ml.

Figure 4:
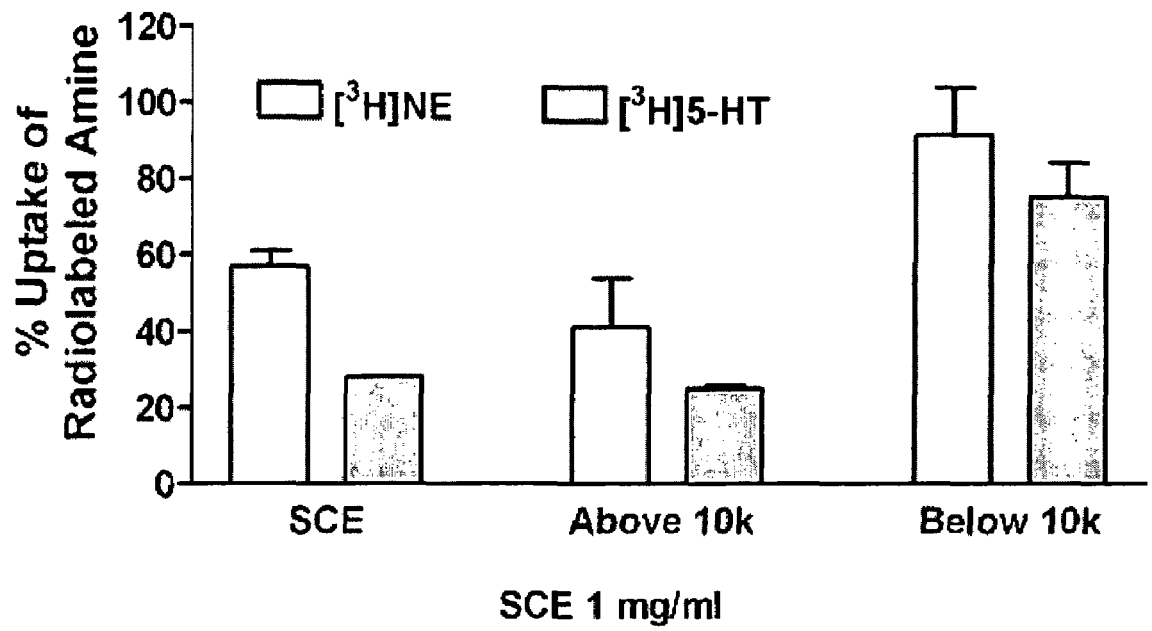
FIG. 4 is a graph showing the inhibiting effects of the present yeast extract on reuptake of [3H]NE and [3H]5-HT in white rat's cerebral cortex synaptosomal membranes.

5-HT and NE was known to play an important role in pathogenesis of depression (Risch et al., 1992). Because the present yeast extract (SCE) and its fractions was found to have affinity to SERT and NET in Experimental Example 1, the effect of SCE and its fractions on uptake of 5-HT and NE via SERT and NET was verified in white rate's cerebral cortex synaptosome sample. All of SCE, Above 10 k and Below 10 k inhibit uptake of 5-HT and NE, which is consistent with results of affinity test (FIG. 4). FIG. 4 is a graph showing the inhibiting effects of the present yeast extract on reuptake of [3H]NE and [3H]5-HT in white rat's cerebral cortex synaptosomal membranes. In the FIG. 4, data is expressed as mean ±SEM, SCE means whole yeast extract, Above-10 k means a fraction with above 10000 Da, Below-10 k means a fraction with below 10000 Da. As seen in FIG. 4, SCE and Below 10K show uptake-inhibition effects, especially Above 10K shows remarkable effects inhibiting uptake of [3H]NE and [3H]5-HT to the level below 40%.

Experimental Example 4

Forced Swimming Test (FST)

Figure 5:
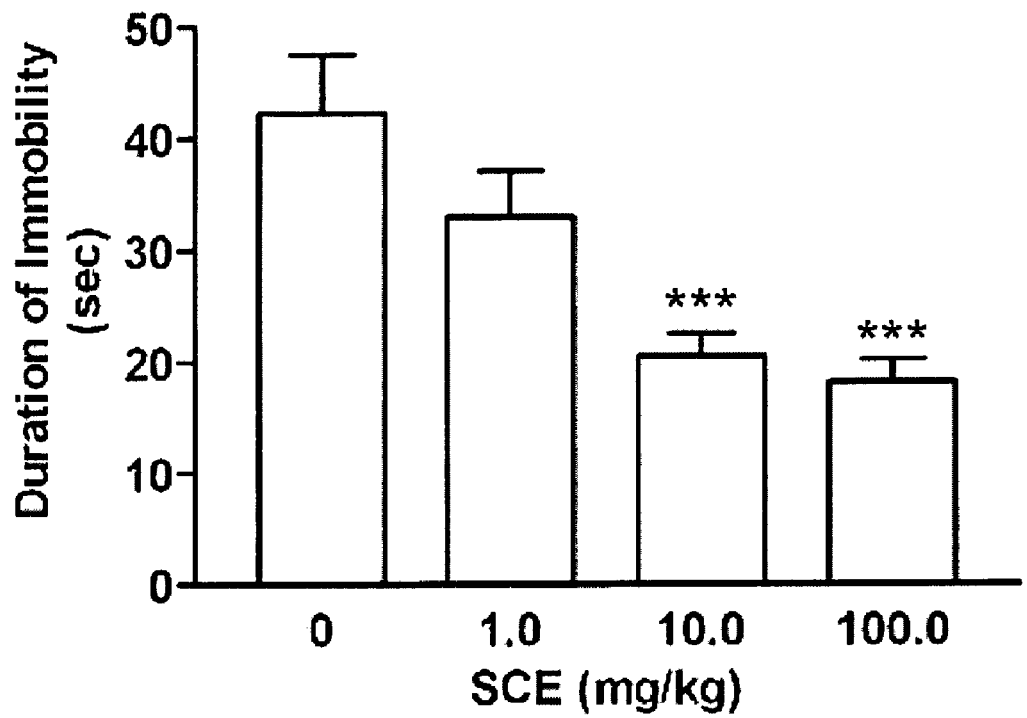
FIG. 5 is a graph showing effect of the present yeast extract on duration of immobility in FST.

To confirm anti-depression effect of the present yeast extract, forced swimming test (FST) was carried out. Forced-swimming test (FST) has been frequently used as test model of depression (Rodrigues et al., 2002). Before carrying out FST, 1, 10 and 100 mg/kg of the present yeast extract (SCE) were orally administered to male ICR mice (30-35 g) for 2 weeks. The mice were put into a transparent vertical cylinder (diameter 10 cm, length 25 cm) filled with 12 cm depth of water at room temperature for 6 minutes. Out of last 4 minutes, total duration of immobility was measured. It is considered as immobility only when the mice stop swimming or float without action. FIG. 5 is a graph showing effect of the present yeast extract on duration of immobility in FST. Data was expressed as mean ±SEM (***: P<0.001). As shown in FIG. 5, the duration of immobility was significantly reduced in the mice administered with 10 and 100 mg/kg of SCE compared with the control group administered with physiological saline.

Figure 6:
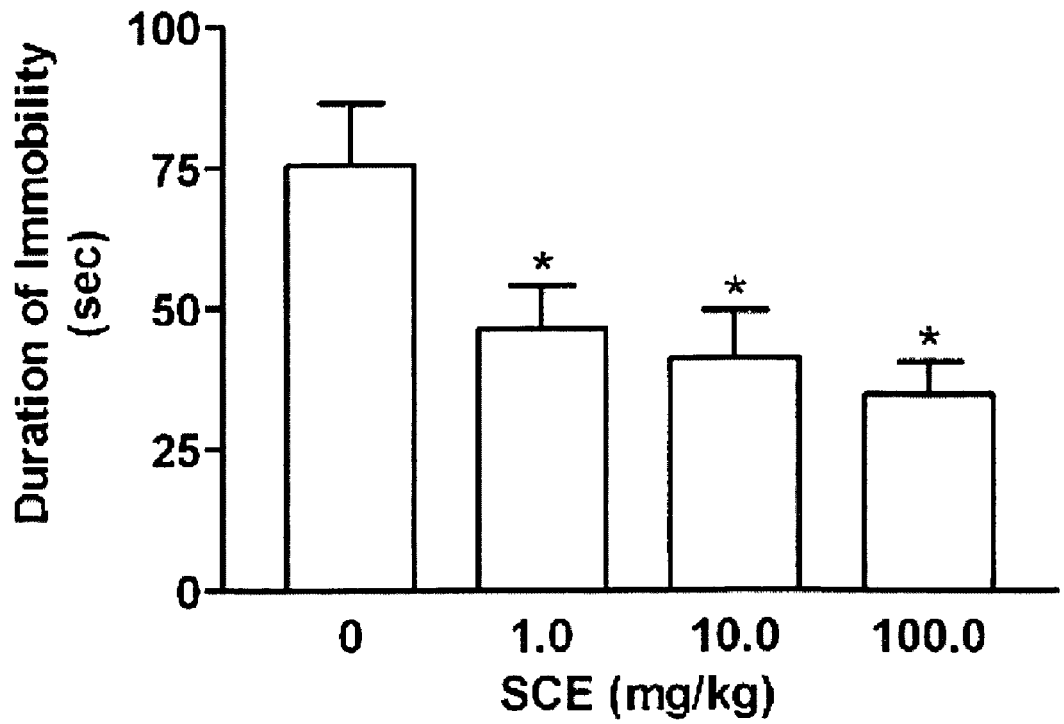
FIG. 6 is a graph showing acute effect of the present yeast extract on duration of immobility in FST.

In addition, to confirm anti-depression effect of the present yeast extract by once administration, FST was carried out 1 hour after administering 1, 10, 100 mg/kg of SCE. FIG. 6 is a graph showing acute effect of the present yeast extract on duration of immobility in FST. Data was expressed as mean ±SEM (*: P<0.05). As shown in FIG. 6, the duration of immobility was significantly reduced in the mice administered with SCE compared with the control group administered with physiological saline. These results verify that both of long and short term administration of SCE can express an anti-depression effect.

Experimental Example 5

Tail Suspension Test (TST)

Figure 7:
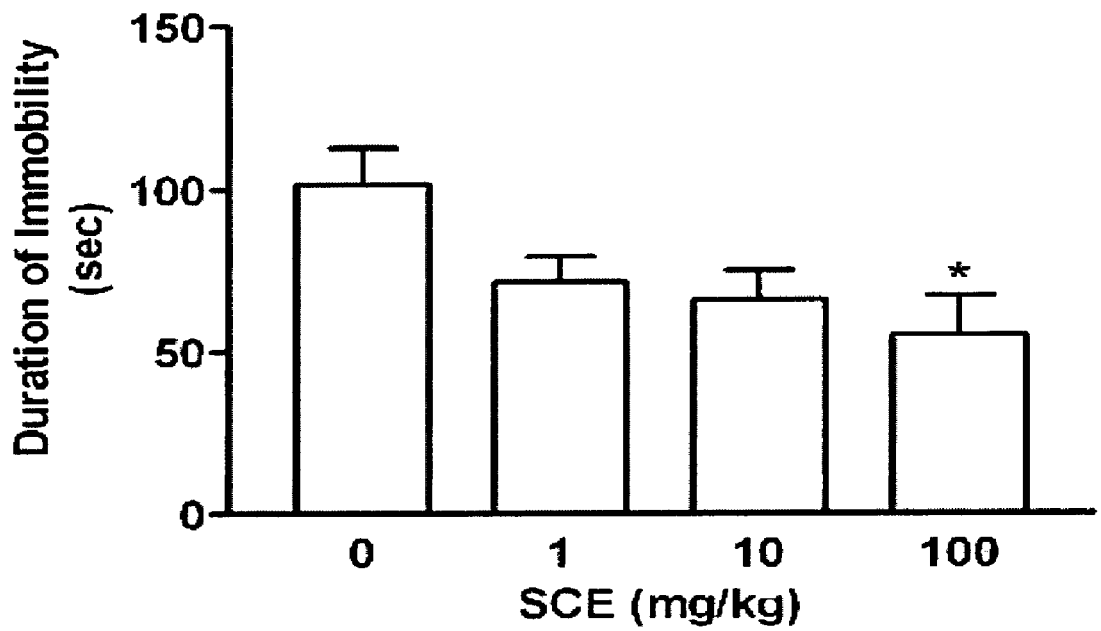
FIG. 7 is a graph showing effect of the present yeast extract on duration of immobility in TST.

To additionally confirm anti-depression effect of the present yeast extract, tail suspension test (TST) was carried out. Tail suspension test (TST) is another behavioral experimental method to test anti-depression effect. Before carrying out TST, 1, 10 and 100 mg/kg of the present yeast extract (SCE) were orally administered to male ICR mice (30-35 g) for 2 weeks. The mice were suspended with their tails fixed at 50 cm of height from the bottom for 6 minutes. Out of last 4 minutes, total duration of immobility was measured. FIG. 7 is a graph showing effect of the present yeast extract on duration of immobility in TST. Data was expressed as mean ±SEM (*: P<0.05). As shown in FIG. 7, the duration of immobility was significantly reduced in the mice administered with SCE compared with the control group administered with physiological saline. This result verifies that the present yeast extract has an anti-depression effect.

Experimental Example 6

Elevated Plus-Maze Test (EPM)

Figure 8:
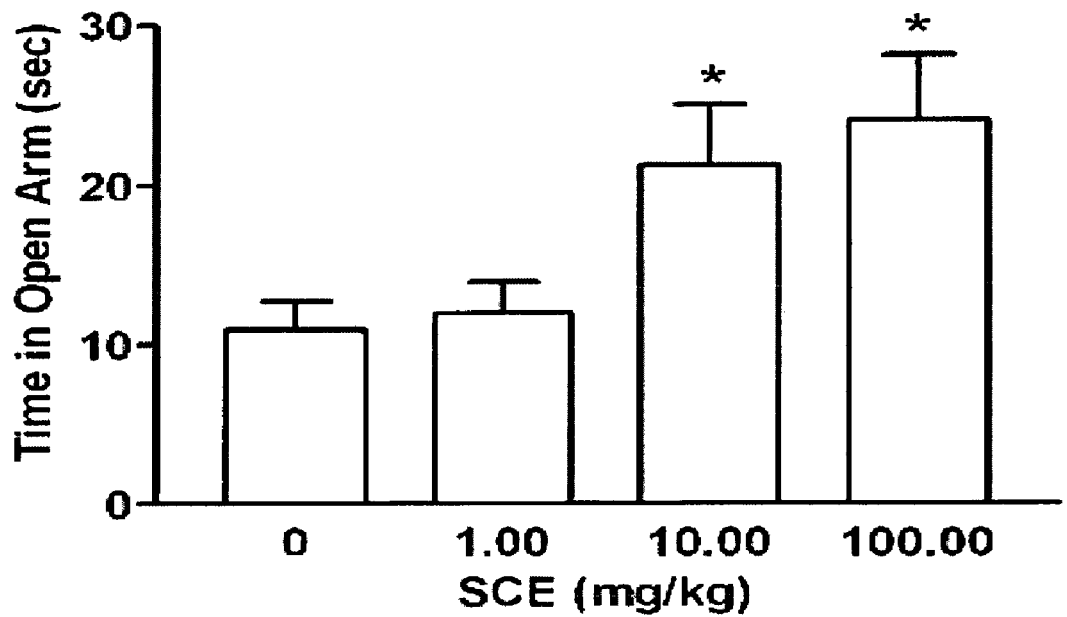
FIG. 8 is a graph showing effect of the present yeast extract on time in open arm in EPM.

To confirm anti-anxiety effect of the present yeast extract, elevated plus-maze test (EPM) was carried out. Elevated-plus maze test (EPM) has been used to verify anti-anxiety effect (Sonavane et al., 2002). Generally, anti-anxiety agents work at the mechanism of serotonin, dopamine, GABA (Gobaille et al., 2002; Eison and Temple, 1986). Before carrying out EPM, 1, 10 and 100 mg/kg of the present yeast extract (SCE) were orally administered to male ICR mice (30-35 g) for 2 weeks. The apparatus for EPM is consisted of two open arms (30×5 cm) and two closed arms (30×5×15 cm) which are crossed over and linked with 5×5 cm of area in the center with barriers having 50 cm height from the bottom. At the beginning, the mice were located in the center and leaved for 6 minutes. Out of last 5 minutes, the number of times passing through the open arms and staying period were measured using a video instrument (SMART, Panlab, Spain). FIG. 8 is a graph showing effect of the present yeast extract on time in open arm in EPM. Data was expressed as mean ±SEM (*: P<0.05). As shown in FIG. 8, the time in open arm was significantly increased in the mice administered with 10 and 100 mg/kg of SCE compared with the control group administered with physiological saline.

Figure 9:
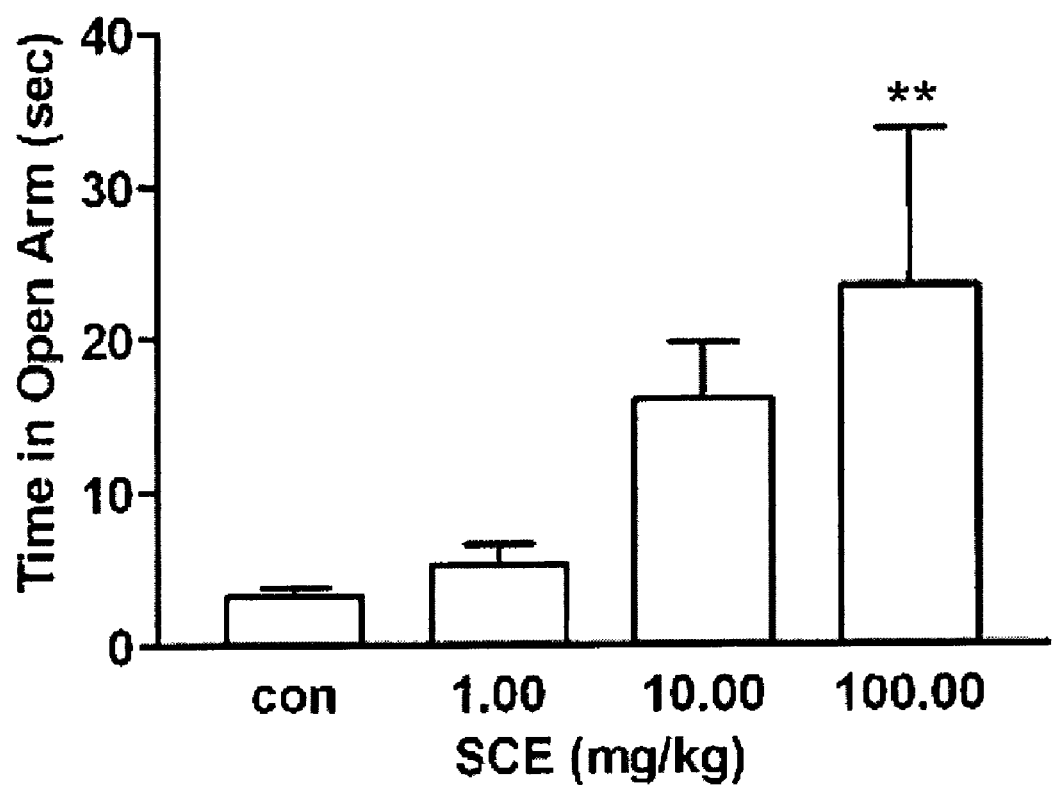
FIG. 9 is a graph showing acute effect of the present yeast extract on time in open arm in EPM.
Figure 10:
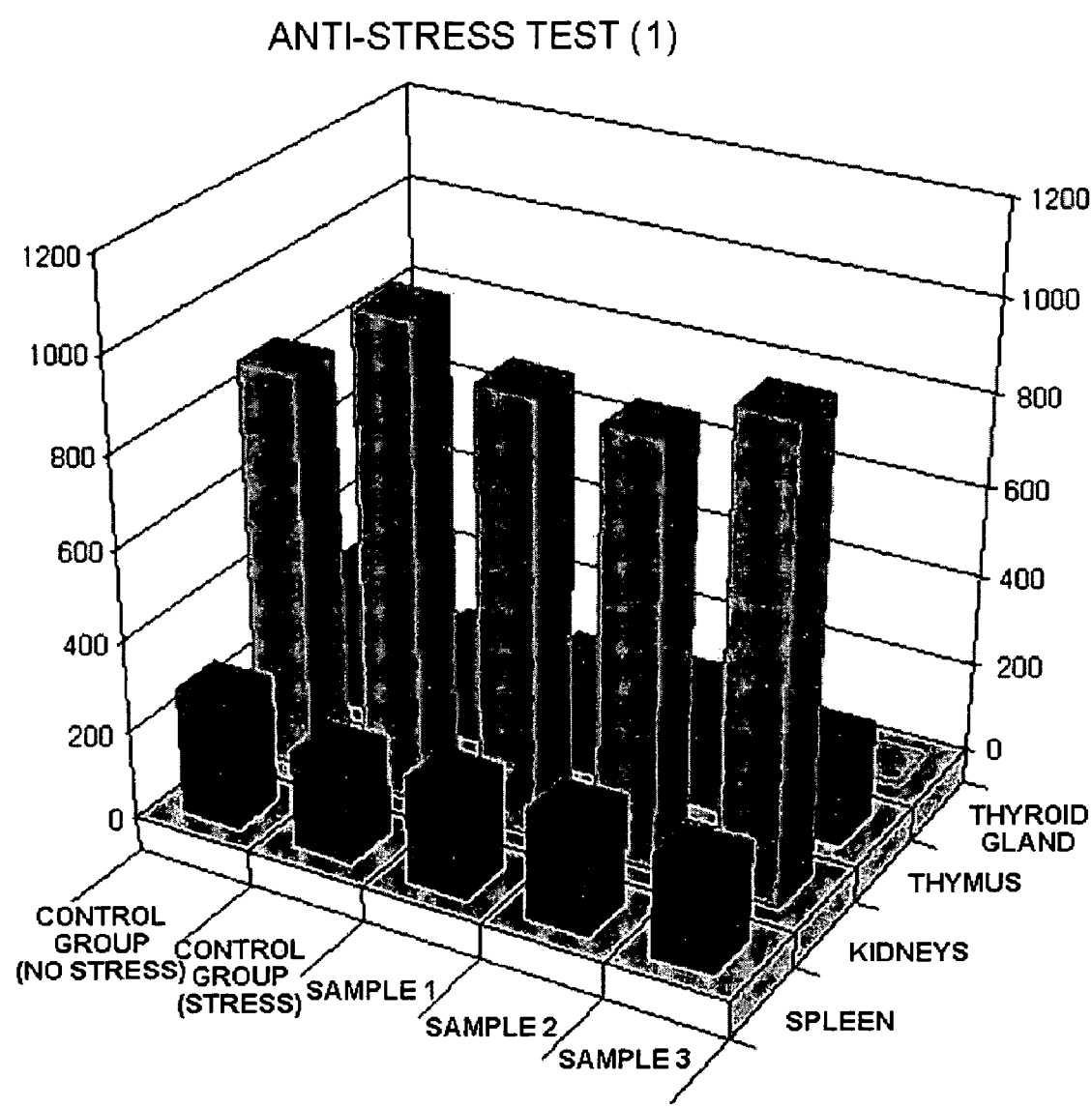
FIG. 10 is a graph of the result of Anti-stress Activity Test (1) for the present invention.
Figure 11:
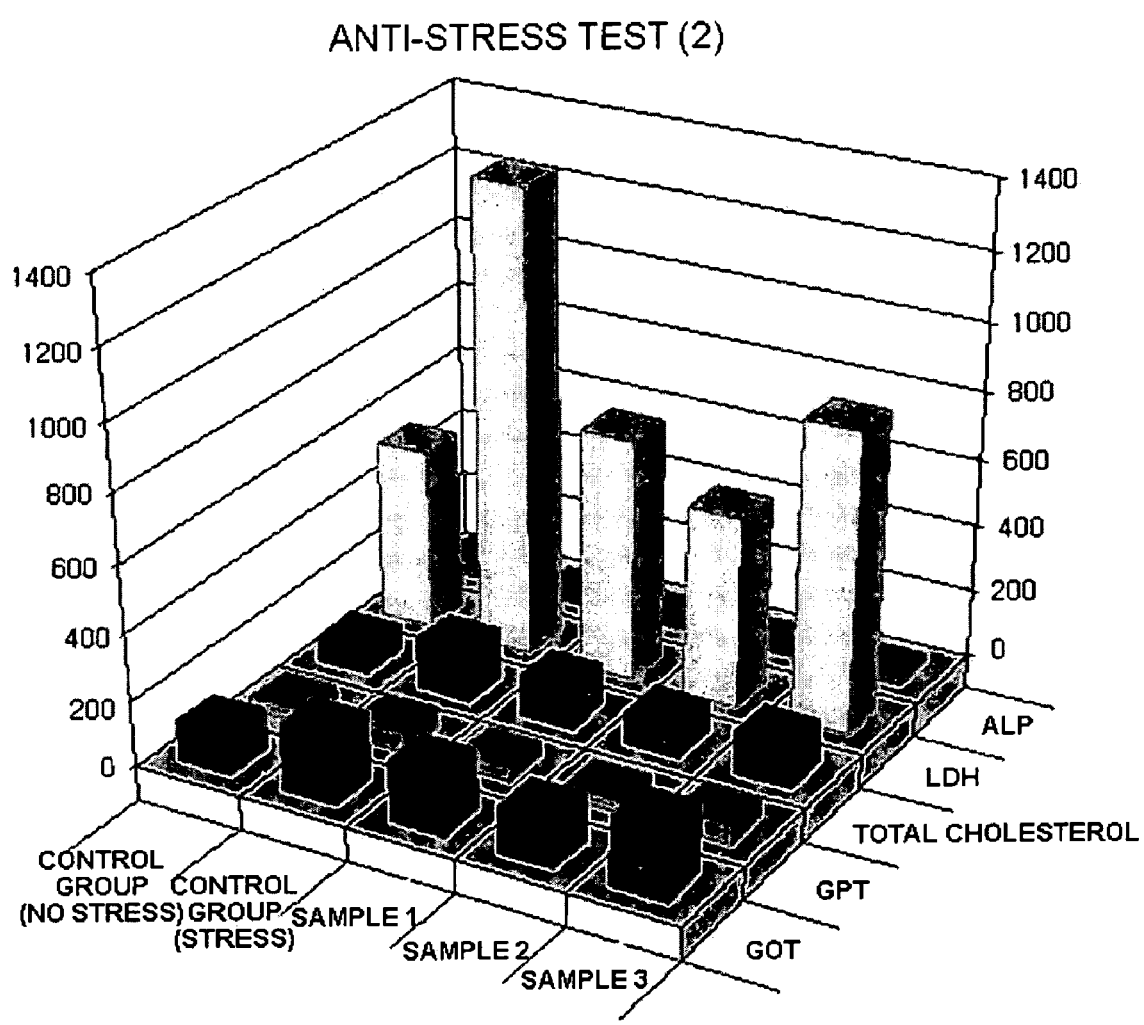
FIG. 11 is a graph of the result of Anti-stress Activity Test (2) for the present invention.

In addition, to confirm anti-anxiety effect of the present yeast extract by once administration, EPM was carried out 1 hour after administering 1, 10, 100 mg/kg of SCE. FIG. 9 is a graph showing acute effect of the present yeast extract on time in open arm in EPM. Data was expressed as mean ±SEM (**: P<0.01). As shown in FIG. 9, the time in open arm was significantly increased in the mice administered with 100 mg/kg of SCE compared with the control group administered with physiological saline. These results verify that both of long and short term administration of SCE can express an anti-anxiety effect.

Experimental Example 7

Anti-Stress Activity Test (1)

By Ph.D. Kyung-mi Kim, Life Science Institute at Korea University

For an anti-stress activity test, five-week old, about 180 g male Sprague-Dawley rats (from Biolink Co.) were adapted for 1 week in a room at a temperature of 18-23° C. through 12-hour illumination (from 7 a.m. to 7 p.m.) each day. The animals received free access to both feed (solid feed from Cheiljedang Co.) and tap water throughout the experiment. Three kinds of samples were used: "Sample 1" prepared through yeast hydrolysis at a high temperature of 50° C. according to the general yeast extract preparation method as in Example 2, "Sample 2" of the supernatant from the centrifugation in Example 3 after yeast hydrolysis following the application of ultrasonic waves and vibrations to induce stress, and "Sample 3" of the precipitate from the centrifugation of Example 3. All of the three samples were freeze-dried and ground for the experiment.

The male Sprague-Dawley rats were orally administered with the samples in distilled water at a dose of 1 g per body weight in kilograms, once a day for eight consecutive days; three rats for each sample. After a 6-day lapse from the administration, each of the rats was moved into a cylindrical can of a 5-cm-width and a 12-cm-length fixed at an angle of 45° to induce stress for 48 hours.

After 3 hours from the final administration, the rats were anesthetized with ether, and the thymus, spleen, kidneys, and thyroid gland were removed. The weights of the organs were measured and compared with untreated control groups which were subjected to stress. The results are shown in Table 6.

As shown in Table 6, great changes in the weight of the organs associated with the production of stress hormones and the immune system for the stressed control group were observed for the stressed control group; the weights of the spleen, and thymus were reduced, and the weight of the kidneys was increased. In contrast, for the rats administered with Sample 1 and Sample 2, reductions in the weights of the spleen, and thymus due to stress were significantly suppressed, and an increase in the weight of the kidneys due to stress is significantly suppressed. Accordingly, both of the yeast hydrolytes (Sample 1) prepared by the general method and the yeast hydrolytes (Sample 2) subjected to stress from the ultrasonic waves and vibrations had an effective anti-stress activity. From this result, it is believed that the high-temperature yeast hydrolysis and autolysis processes themselves may induce stress, as when the ultrasonic waves or vibrations are intentionally applied.

Experimental Example 8

Anti-Stress Activity Test (2)

By Ph.D. Kyung-mi Kim, Life Science Institute at Korea University

Stress is known to increase the size of the immune organs, including the spleen, to reduce the number of lympocytes, and to alter blood enzyme level, for example, lactate dehydrogenase (LDH) in blood. Also, an increase in blood corticosteroid level due to stress affects lipid metabolism, thereby elevating blood cholesterol level. Based on this fact, the activities of LDH, glutamate oxaloacetate transaminase (GOT), glutamate pyruvate transaminase (GPT), and alkaline phosphatase (ALP) and total cholesterol level in serum were measured to verify the samples according to the present invention for anti-stress effects. The results are shown in Table 7.

TABLE 6

| Sample | Spleen (mg/100 g of body weight) | Kidneys (mg/100 g of body weight) | Thymus (mg/100 g of body weight) | |
|---|---|---|---|---|
| Control Group (No Stress) | 279.28 ± 10.24 | 876.62 ± 19.79 | 313.89 ± 21.69 | |
| Control Group (Stress) | 216.13 ± 6.77* | 1043.83 ± 55.31 | 221.14 ± 21.53 | 5.36 ± 0.47* |
| Sample 1 | 234.11 ± 5.31[b] | 945.18 ± 9.95[a] | 236.51 ± 29.29 | 7.06 ± 0.59[a] |
| Sample 2 | 243.82 ± 16.28[a] | 922.26 ± 11.93[a] | 251.43 ± 3.83 | 5.71 ± 0.34 |
| Sample 3 | 226.43 ± 1.84[b] | 1020.18 ± 44.04 | 211.41 ± 10.30 | |

*, **Significantly different from no-stress control group at p < 0.05 and p < 0.01, respectively.
[a,b]Significantly different from stressed control group at p < 0.1 and p < 0.05, respectively.

TABLE 7

| Sample | Serum GOT | Serum GPT | Serum Total Cholesterol | | Serum ALP |
|---|---|---|---|---|---|
| Control Group (No Stress) | 124.18 ± 2.64 | 40.62 ± 1.99 | 81.03 ± 6.08 | 538.07 ± 66.39 | 48.97 ± 8.05 |
| Control Group (Stress) | 203.6 ± 59.70** | 58.14 ± 3.51 | 154.32 ± 9.73** | | 12.57 ± 1.29** |
| Sample 1 | 182.24 ± 21.73 | 43.10 ± 5.09 | 125.0 ± 81.51[a] | 718.40 ± 59.18[a] | 15.15 ± 1.08 |
| Sample 2 | 141.63 ± 3.79[a] | 31.50 ± 2.07 | 100.59 ± 1.56[b] | 562.40 ± 58.02[a] | 17.10 ± 0.90[a] |
| Sample 3 | 212.69 ± 10.61 | 55.37 ± 3.37 | 129.04 ± 20.87 | | 19.10 ± 1.00[a] |

*, **Significantly different from no-stress control group at $p < 0.05$ and $p < 0.01$, respectively.
[a,b]Significantly different from stressed control group at $p < 0.05$ and $p < 0.01$, respectively.

As shown in Table 7, serum and total cholesterol levels were elevated by the application of stress whereas increases in those levels were significantly reduced by the administration of the samples according to the present invention. Also, the activities of the serum transaminases were elevated by the application of the stress, but were significantly lowered, especially for GOT level, by the administrations of Sample 1 and Sample 2 as compared to the stressed control group. Serum ALP activity was significantly lowered by the stress, but that reduction was significantly suppressed by the administration of Samples 1, 2, and 3.

These results support that Samples 1 and 2 according to the present invention show high anti-stress activities, especially Sample 2.

Experimental Example 9

Anti-Fatigue Activity Test

By Ph.D. Kyung-mi Kim, Life Science Institute at Korea University

Figure 12:
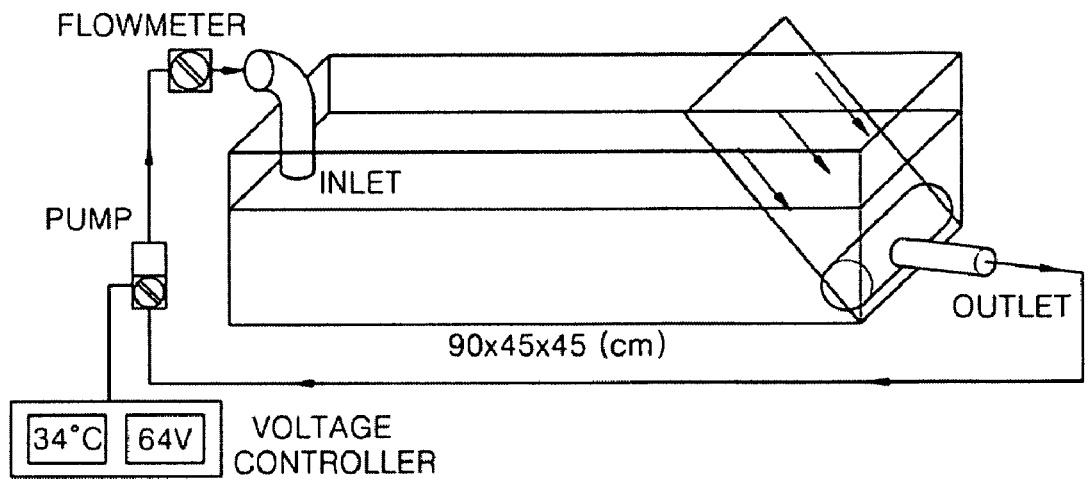
FIG. 12 shows an experimental swimming pool used to measure mouse' swimming endurance as a measure of anti-fatigue effects.

As another measure of the anti-stress activity of the yeast extract according to the present invention, the anti-fatigue activity of the yeast extract was determined by measuring swimming endurance, which is believed to be related to anti-stress effects. A swimming endurance test was conducted using an experimental swimming pool (Matsumoto et al, 1996), as shown in FIG. 12. Seven-week old, about 128 g male ICR mice (from Korean International Experimental Animal Center) were adapted for 1 week, three per cage (33×23×12 cm) in a room at a temperature of 22-24° C. and 50% humidity through 12-hour illumination (from 7 a.m. to 7 p.m.) each day. The animals received free access to both feed (solid feed from Cheiljedang Co.) and tap water throughout the experiment. A control group of mice was orally administered with the feed alone at a dose of 1 g per kilogram of body weight, and an experimental group of mice was orally administered with the yeast extract at a dose of 1 g per kilogram of body weight prepared by yeast hydrolysis at a high temperature of 50° C., as in Example 2. The swimming endurance test was performed three times over 9 days. The number of mice in each of the control and experimental groups was six. For the swimming endurance test, the acrylic plastic swimming pool (90×45×45 cm) shown in FIG. 12 was filled with water to a 35-cm-depth and maintained at 34° C. and a water flow rate of 8 L/min. Here, the flow of water was induced by controlling the voltage of a pump using a voltage controller and maintained constant using a flowmeter (Type F45500, Blue White Co., Westmister, Calif., USA).

To minimized deviations in the physical activities of the mice and experimental data, the swimming endurance test was performed in the period of time from 1 p.m. to 5 p.m. The limit of swimming time of the mice was counted from the point of time after a 7-second lapse from observing the mice sink into the water. The swimming time was determined to be the period of time from the start of swimming to that time limit (Matsumoto et al., 1966). The results are shown in FIG. 13.

Figure 13:
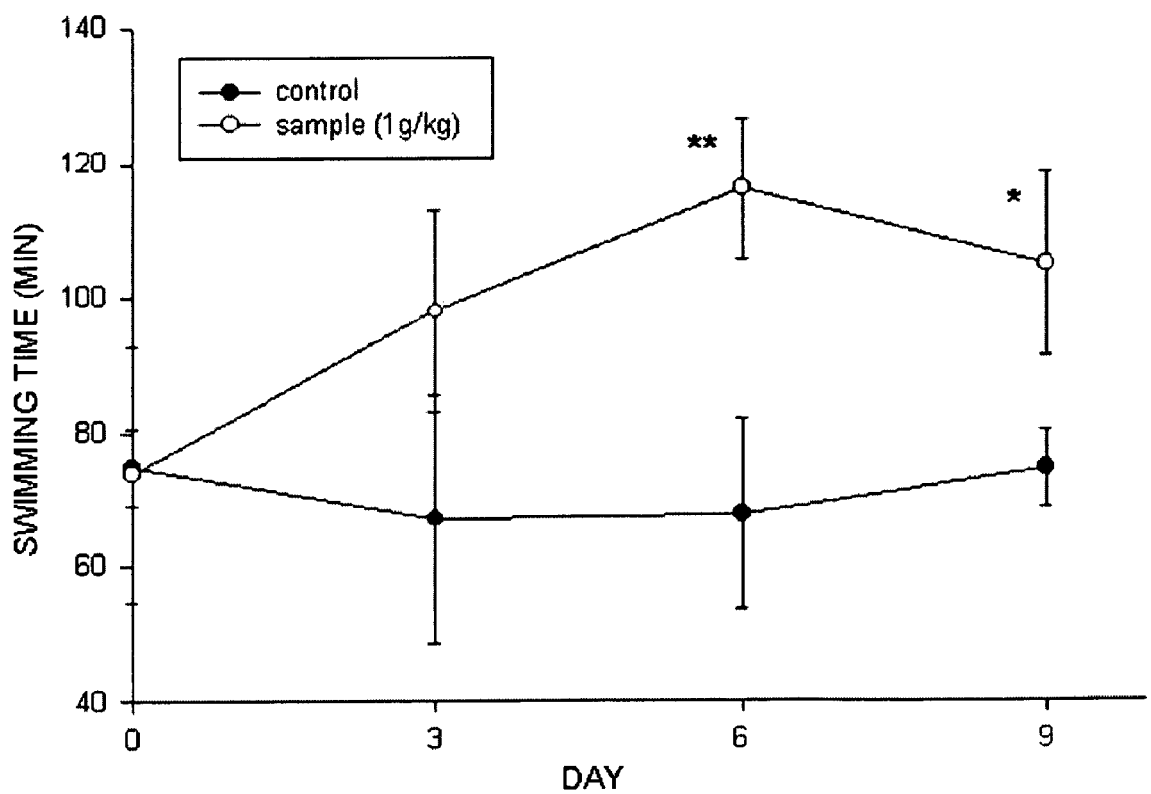
FIG. 13 is a graph of the result of an anti-fatigue activity test for the present invention.

As shown in FIG. 13, the swimming time was markedly prolonged for the experimental group orally administered with the yeast extract according to the present invention, compared to the control group. This result verifies the yeast extract according to the present invention has anti-fatigue and anti-stress activities.

Experimental Example 10

Autonomic Nerve Regulation Activity Test

The yeast extract prepared in Example 2 was given to patients with anxiety for an autonomic nerve regulation activity test. In general, stress endurance is closely associated with the flexibility of the sympathetic nerve and parasympathetic nerve. Accordingly, heart rate variability is measured for a significant index of stress endurance, TP. The index of TP means the total power over the very low frequency (VLF), low frequency (LF), and high frequency (HF) bands during a 5-minute heart rate variability measurement, and reflects the overall activity of the autonomic nervous system, including the sympathetic nerve directly affected by stress. The result of this measurement is shown in FIG. 14. The autonomic nerve regulation activity was apparent in the experimental group treated with the yeast extract of the invention whereas no great difference in TP in the control group given a placebo. This increased activity in the autonomic nerve regulation supports that the ability to endure in stress and the ability to regulate other pain-inducing substances can be enhanced by the yeast extract according to the present invention. Therefore, it is believed that the yeast extract according to the present invention would be effective in alleviating PMS causing stress and pains.

Experimental Example 11

Bone Marrow Cell Proliferating Activity Through Peyer's Patch

The activity was measured in accordance with the procedure of Hong et al.[15] Yeast hydrolysate of present invention from *Saccharomyces cerevisiae* was administered orally into C3H/HeJ mice (Daehan Biolink Co., Korea) at different doses, and the mice received distilled water alone as the control. After the oral administration for 7 consecutive days, suspensions of Peyer's patch cells in RPMI 1640 medium supplemented with 5% FBS (RPMI 1640-FBS) were prepared from the small intestine of C3H/HeJ mice. Two hundred μl of aliquots of the cell suspension ($2\times10^6$ cells/ml) were cultured for 5 days at 37° C. in a humidified atmosphere of 5% $CO_2$-95% air. The resulting culture supernatant (50 μl) was incubated with bone marrow cell suspension ($2.5\times10^5$ cells/ml) from untreated C3H/HeJ mice for 6 days in the same incubator. After 20 μl of ALAMARBLUE™ solution was added and the cells were then continuously cultured for 5-24 hours, the fluorescence intensity was measured to count cell numbers by SPECTRAFLUOR Plus (Tecan, Austria) at an excitation wavelength of 544 nm and an emission wavelength of 590 nm during cultivation.

Figure 15:
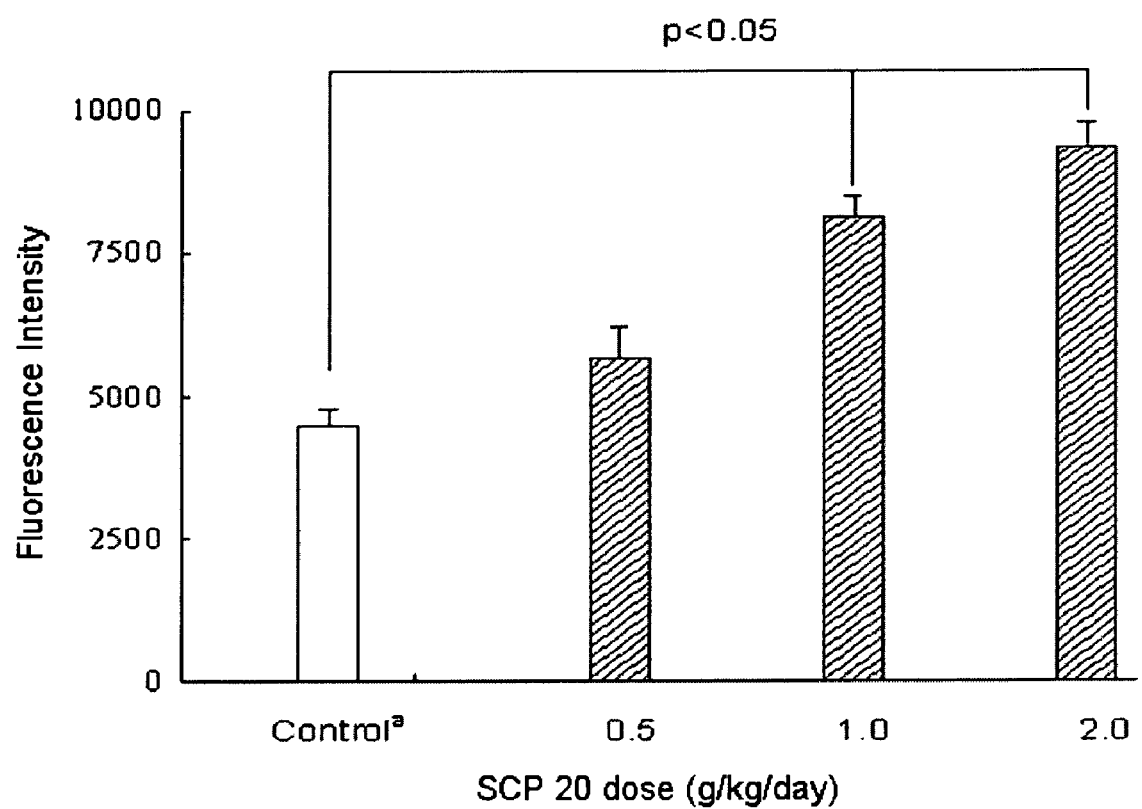
FIG. 15 is a graph showing the degree of bone marrow cell proliferation with respect to different doses of the yeast-derived peptide according to the present invention.

Bone marrow cells were proliferated in a dose-dependent manner and reached almost plateau over 2.0 g/kg per day, as shown in FIG. 15. When 2.0 g/kg per day of yeast hydrolyte of this invention was used for stimulation of Peyer's patch cells, the number of bone marrow cells increased up to 2.1-fold measured by ALAMARBLUE™ reduction assay (FIG. 15). This observation suggests that several kinds of growth factors may contribute to the proliferative response. Lymphocytes, such as typically activated T cells, are known to secrete growth factors such as IL-6,[24] and these growth factors stimulate proliferation of hematopoietic cells and follow by differentiation to granulocytes or macrophages. In order to know whether yeast hydrolyte of this invention enhances IL-6 secretion from Peyer's patch cells, Peyer's patch cells of C3H/HeJ administered the yeast hydrolyte 7 days at different doses were cultured for 5 days, and then levels of IL-6 were examined. The IL-6 content increased in the conditioned medium significantly when Peyer's patch cells were administered with the yeast hydrolyte (at 2.0 g/kg per day, 2.3-fold) (Table 8). These results suggest that IL-6 may contribute to the proliferation of bone marrow cells in a part. Because IL-6 is a multifunctional hematopoietic growth factor, they stimulate the granulopoiesis.

TABLE 8

Effect of Orally Administered Hydrolyte from
*Saccharomyces cerevisiae* on IL-6 in the Culture Supernatant of Peyer's Patch Cells and Macrophages

| Sample | Dose | Relative content of IL-6 (%) | |
|---|---|---|---|
| | (g/kg per day) | Peyer's patch[b] | Macrophage[c] |
| Control[a] | — | 100 ± 3.4 | 100 ± 4.3 |
| Yeast hydrolyte | 0.5 | 122 ± 2.5* | 119 ± 3.8* |
| | 1.0 | 188 ± 5.7* | 165 ± 10.6 |
| | 2.0 | 231 ± 9.7* | 187 ± 8.6* |

[a]Saline alone was administered for control.
[b]Peyer's patch cells were obtained from C3H/HeJ mice (n = 4) fed SCP-20 at different doses for 7 days, and pooled and cultured at a density of $4 \times 10^5$ cells/well for 5 days in vitro. The resulting cell-free supernatants were subjected to ELISA for IL-6.
[c]Macrophage cells were obtained from ICR mice (n = 4) fed SCP-20 at different doses for 7 days, and pooled and cultured at a density of $2 \times 10^5$ cells/well for 2 days in vitro. The resulting cell-free supernatants were subjected to ELISA for IL-6.
*Significant difference between control and samples at $p < 0.05$.
Data were expressed as percent of control of mean ± S.D. of quadruplicate assays.

Experimental Example 12

Macrophage-Stimulating Activity and the Production of IL-6

1) Macrophage-Stimulating Activity

Male ICR mice (from Daehan Biolink Co., Chungcheongbuk-Do, Korea), which had been orally administered with yeast hydrolyte of the invention at different doses, are injected aseptically with 1 ml of 3% thioglycollate broth via i. p. Peritoneal exudates cells were harvested by the injection of 5 ml of the cold RPMI-1640 medium (Gibco, Grand Island, N.Y.) containing 5 mM HEPES, penicillin (100 U/ml) and streptomycin (100 μg/ml). After the cells suspension was adjusted to $1\times10^6$ cells/ml and incubated at 37° C. in a humidified chamber (48 h), the macrophage-stimulating activity was measured using an assay system of the cellular lysosomal enzyme based on the activity of acid phosphatase from macrophages (Bio-Rad, Model 3550-UV).

2) Determination of IL-6 in Supernatant of Macrophage and Peyer's Patch Cell Cultures The ELISA (enzyme-linked immunosorbent assay) employing the multiple antibody sandwich principle was used. After 2 μg of purified anti-mouse IL-6 mAb (monoclonal antibody) (clone MP5-20F3, PharMingen, San Diego, Calif.) in 50 μl of bicarbonate buffer (pH 8.5) was adhered to each well of 96 plates, unbound antibody was removed by washing 4 times with PBS containing 0.05% Tween 20 (PBS-Tween). Samples were added to the antibody-coated wells at a 100 μl, and each 100 μl of biotinylated anti-mouse IL-6 mAb (MP5-32C11, PharMingen) in PBS containing 10% FBS was added to the same wells. After the plates were washed 6 times with PBS-Tween, alkaline phosphatase-labelled streptoavidin (Gibco, Grand Island, N.Y.) was added to each well. Each well was incubated with 150 μl of chromogenic substrate solution (1 mg of p-nitrophenyl disodium salt in 1 ml of 10% diethanolamine buffer, pH 9.8), and subsequently the absorbance at 405 nm was measured.

Statistical analysis: All results were expressed as the mean ±S.D. The difference between the controls and the treatments in these experiments was tested for statistical significance by Student's t-test. A value of $p<0.05$ was considered to indicate statistical significance.

3) Result

Figure 16:
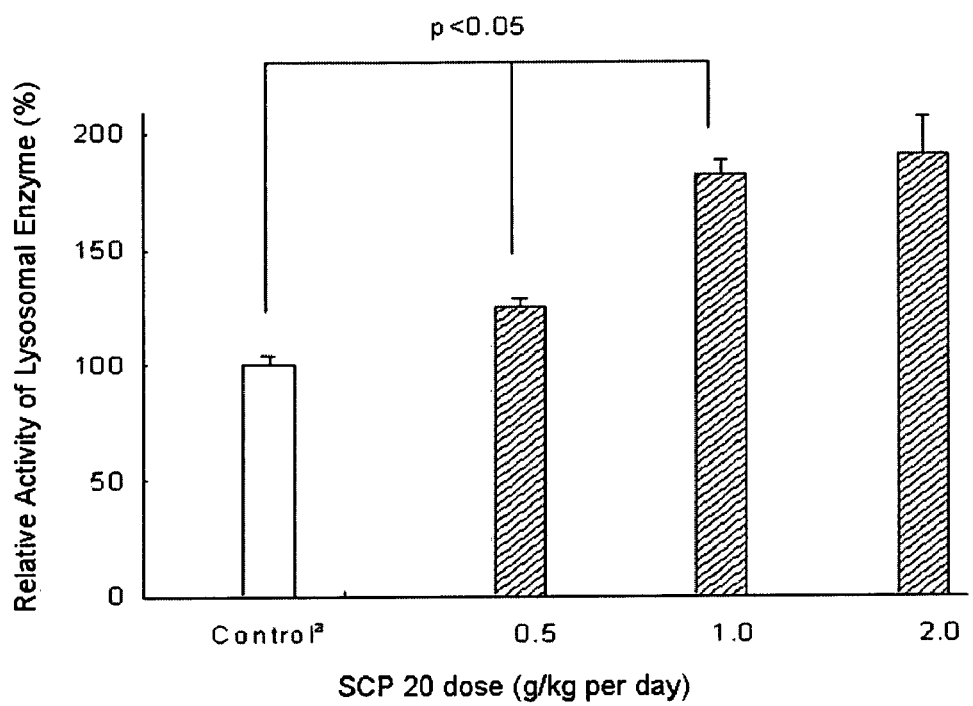
FIG. 16 is a graph showing the relative activity of a macrophage lysosomal enzyme with respect to different doses of the yeast-derived peptide according to the present invention.

Administration of 0.5, 1.0 and 2.0 g/kg per day of yeast hydrolyte of the invention for 7 days revealed a dose-dependent increase in the relative activity of a macrophage lysosomal enzyme, as shown in FIG. 16. A significant increase in the relative activity was seen at 0.5 g/kg per day (1.3-fold of saline control), and maximum stimulation was made by 2.0 g/kg per day (1.9-fold) (FIG. 16). These results suggest that the oral administration of yeast hydrolyte of the invention enhance the stimulatory responses of macrophages. In addition, the effects of the orally administered yeast hydrolyte of the invention at different doses on IL-6 secretion, which enhances IL-2 production from T cell and stimulates proliferation of hematopoietic cells, from macrophages were investigated in mice. Oral administration of the yeast hydrolyte of the invention was found to increase significantly and dose-dependently, compared to the control, and the yeast hydrolyte of the invention stimulated the most IL-6 production at 2.0 g/kg per day (1.9-fold) (Table 8).

For activation of a macrophage function, at least one signal must be provided.[27] The signal, which sensitizes the macrophage to respond to the other signal, is delivered by the macrophage stimulating cytokine IFN-γ.[28] IFN-γ is the most specific cytokine produced by Th1, Tc and natural killer cells.

It does not induce macrophage cytokine production but it regulates macrophage cytokine production, which is enhancing the production of IL-1, IL-6 and TNF-α. The cytokine network of macrophage plays an important role in the inflammatory and immune responses, and especially, IL-6 is significant in the differentiation and as growth factor of macrophage.

From this experiment, it is believed that oral administration of the yeast hydrolyte of the invention hydrolyzed from *Saccharomyces cerevisiae* may modulate IL-6 production in macrophage. Enhancement in the production of the cytokine, IL-6 by the oral administration of the yeast hydrolyte of the invention suggests that the yeast hydrolyte of the invention might induce the activation of macrophage. In addition, oral administration of the yeast hydrolyte of the invention is believed to enhance secretion of hematopoietic growth factors from Peyer's patch cells. Since Peyer's patch cells are mainly composed of T and B cells, and T cells are known as a source of CSFs and various cytokines as well as macrophages, T cell activation, which is caused by oral administration of the yeast hydrolyte of the invention, may contribute to secretion of hematopoietic growth factors such as IL-6 from Peyer's patch cells. Especially, since the cytokines such as IL-6 is important in the systemic immunocytes, the orally administered yeast hydrolyte of the invention would regulate the systemic immune system according to the Peyer's patch-mediated mechanism.

Therefore, studies on fractionation and purification-activity relationship of these active substances, yeast hydrolyte of the invention, on biological activity will give useful important information.

Experimental Example 13

Clinical Test

By Neuropsychiatrist Won-jun Hwang

To verify the anti-stress effect of the present invention in the human body, a clinical test was performed on three groups of patients with neuropsychiatric problems: a group with insomnia, a group with anxiety, and a group with headaches.

Baseline brain mapping was performed on those groups of patients after a 3-day postadministration (Feb. 6, 2001). After 3-day administration of the yeast extract according to the present invention at a dose of 500 mg a day, the brain mapping was conducted (Feb. 9, 2001). The results are shown in FIGS. 14A and 14B.

Figure 14A:
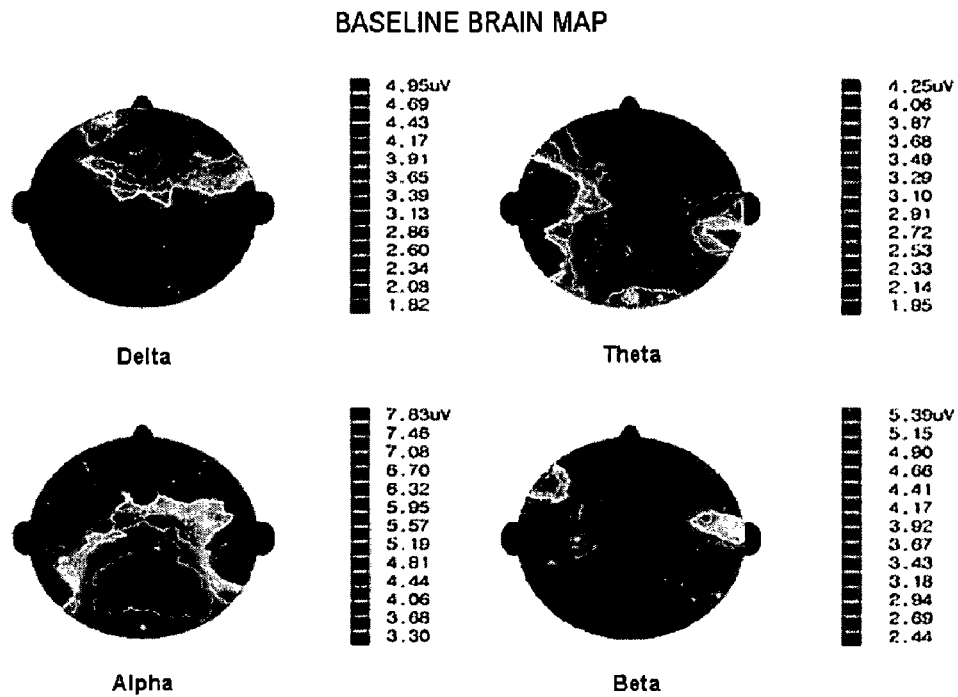
FIGS. 14A and 14B are brain maps obtained as a result of a clinical test for the anti-stress effect of the present invention.
Figure 14B:
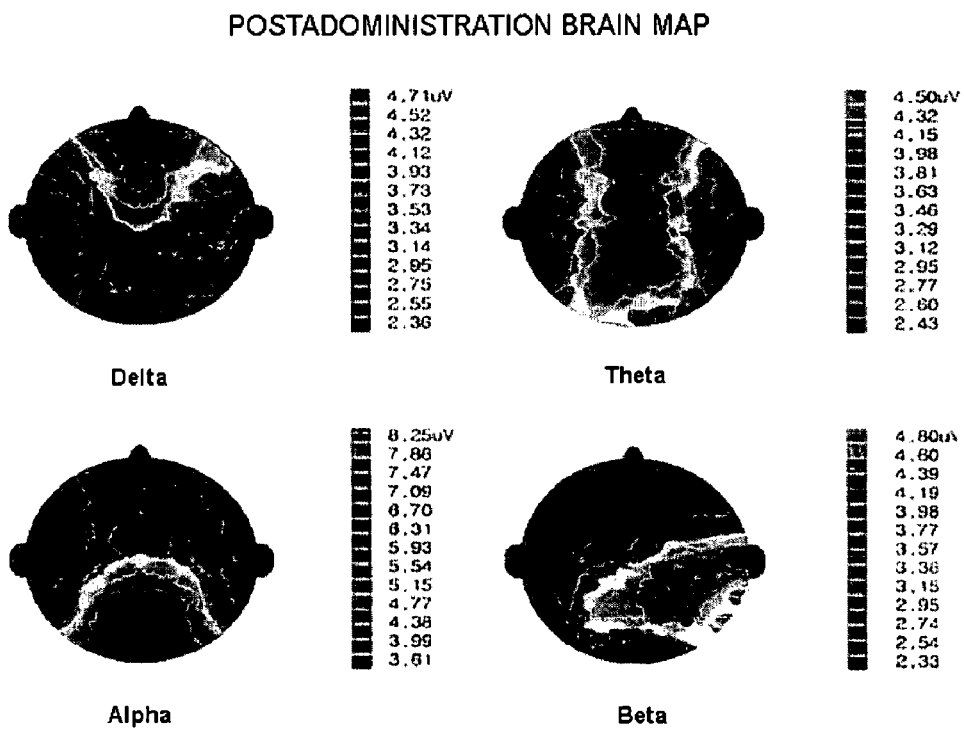

As shown in FIGS. 14A and 14B, as a result of the baseline brain mapping, an asymmetric increase in theta wave activity was observed in almost all the brain region. This increased theta wave activity means a psychic tension state due to increased mental activity. In contrast, after the administration of the yeast extract according to the present invention for 3 days, a symmetrical distribution of the theta wave in the central and parietal lobes was observed. This pattern of theta wave distribution appears in a psychologically stable state such as when one is completely relaxed or in a hypnotic or hypnagogic stage.

Experimental Example 14

Clinical Test

By Neuropsychiatrist Won-jun Hwang

Capsules prepared in Example 5 were orally administered 2-3 times a day, 1-2 capsules each, given to thirty women in 20-35 ages with PMS, menstrual pains, or hysterorrhea before their menstrual cycle or for menstrual pains during the menstrual cycle.

The subjects were asked for thirty questions about changes after the administration, ten relating to physical symptoms, ten relating to emotional symptoms, and ten relating to behavior symptoms. The thirty questions were:

A) Physical Symptoms
1) Asthenia or fatigue
2) Increased or decreased appetite
3) Breast fullness or tenderness
4) Headaches
5) Nausea or vomiting
6) Dizziness or giddiness
7) Swelling
8) Abdominal aches or unwell and intermittent abdominal cramping
9) Insomnia
10) Changes in sexual relationship or in interests B) Emotional Symptoms
1) Serious mood swings in a day
2) Be anxious or agitated
3) Be nervous or restless
4) Be sad or depressed
5) Nag or quarrel over a trivial matter
6) Be hysteric or irritable
7) Feel guilty
8) Be unappreciative or impatient with others' defects or mistakes
9) Think over or worry about discomforting matters
10) Be blunt C) Behavioral Symptoms
1) Be slow in or poor at movement
2) Often make a mistake or causes an accident (e.g., falls over, gets a cut from a knife, or breaks something by mistake)
3) Think about death or self-murder (e.g., wants to be dead and gone in sleep)
4) Be unwilling to speak or go out
5) Abuse drugs (excitant, sedative, etc.) or smoke or drink heavily
6) Be rude or behave annoyingly
7) Decreased efficiency or activity at home and office
8) Avoid social activities and want to stay at home
9) Too lazy to do domestic duties (cleaning, washing, etc.)
10) Have less leisure hours (hobbies, watching TV, reading, etc.)

The subjects were asked to answer each of the questions and grade the degree of each symptom on a 6-point scale: 1 for none, 2 for almost none, 3 for slight, 4 for moderate, 5 for fairly severe, and 6 for extremely severe. In addition, the overall feeling before and after the administration and pain relaxation time and its duration were asked. The average of those scores from the subjects for each symptom was calculated.

As a result, pain relaxation appeared within 10 minutes at the earliest and 1 hour at latest, with a duration of about 4-6 hours. PMS alleviation was significant in all of the physical, emotional, and behavioral symptoms. The average degree of each symptom before and after the administration and its variation are shown in Table 9.

TABLE 9

| Symptom | Before | After | Variation |
| --- | --- | --- | --- |
| Physical Symptoms | 32 | 23 | 9 |
| Emotional Symptoms | 30 | 24 | 6 |
| Behavioral Symptoms | 29 | 22 | 7 |
| Overall Symptoms | 91 | 69 | 22 |

It was found that the PMS and menstrual pain relaxant composition according to the present invention can effectively relieve severe pains, paralysis, indigestion, and vomiting before or during the menstrual cycle and can activate blood circulation and improve temper. Most of the female subjects answered that their pessimistic and depressed mood disappeared after taking the PMS and menstrual pain relaxant composition according to the present invention. Furthermore, the PMS and menstrual pain relaxant composition according to the present invention was known to be effective against lumbago during menstruation. A woman with serious lumbago answered that her lumbago disappeared within 30 minutes after taking 2 capsules (each containing 180 mg of the PMS and menstrual pain relaxant composition according to the present invention) in favor of future administrations. Women with the inability to fall into deep sleep or those who experience sleep interruptions due to their menstrual pains were able to sleep deeply after the administration of the PMS and menstrual pain relaxant composition according to the present invention. Unlike conventional analgesia that completely kill pains by causing paralysis and unconsciousness, the PMS and menstrual pain relaxant composition according to the present invention does not cause unconsciousness although there remains a mild but not bad pain. However, most of the female subjects preferred the PMS and menstrual pain relaxant composition according to the present invention to conventional analgesia. Also, the effect of warming of the abdomen and extremities was observed in most of the female subjects. The PMS and menstrual pain relaxant composition according to the present invention was more effective in women who took the composition before menstruation. For women who took the PMS and menstrual pain relaxant composition according to the present invention after pains had occurred, the pain relaxation effect appeared about 3-4 hours later, on average. Some of the female subjects who had endured pains without taking analgesia due to its medical side effects responded that they will take the PMS and menstrual pain relaxant composition according to the present invention, which is derived from a food source, to enhance their health and alleviate pains, instead of conventional medicinal analgesia.

Experimental Example 15

Clinical Test for Treating Depression and Anxiety

Figure 17:
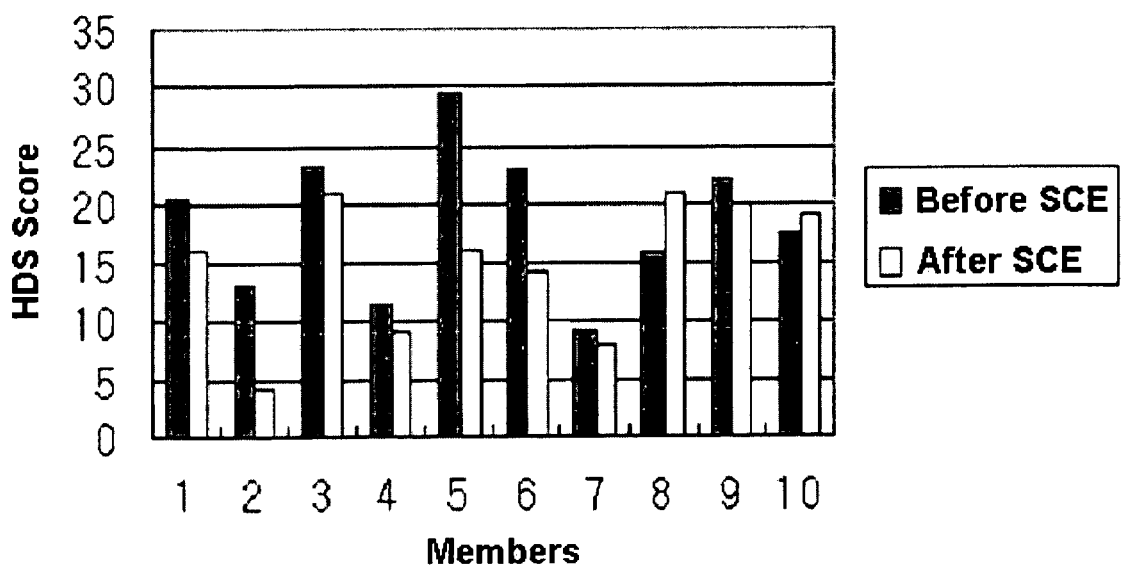
FIG. 17 is a graph showing anti-depression effect of the present yeast extract in HDS.
Figure 18:
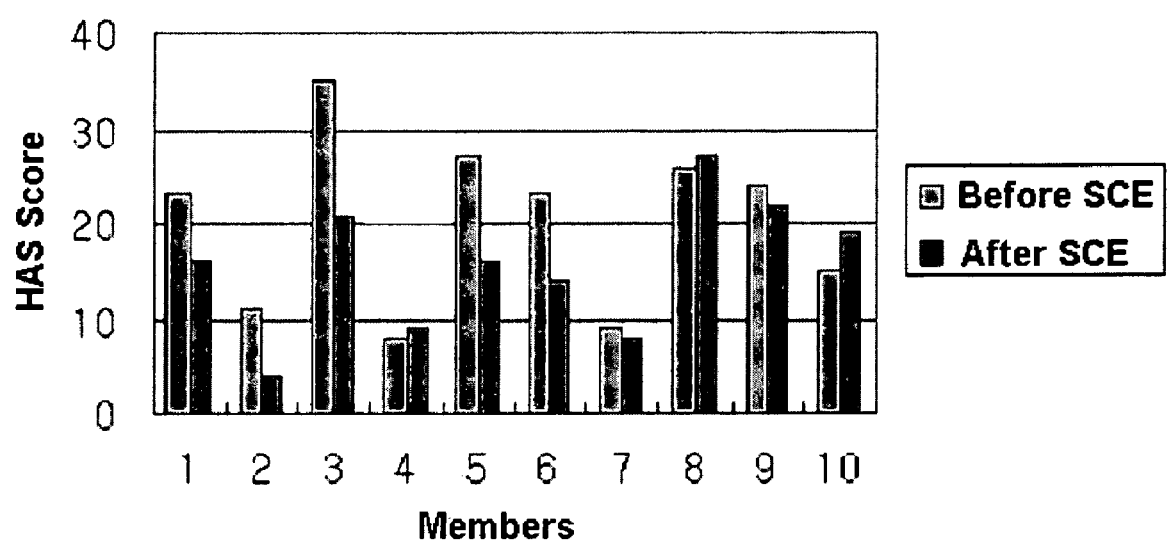
FIG. 18 is a graph showing anti-anxiety effect of the present yeast extract in HAS.

For clinical test on anti-depression and anti-anxiety effects of the present yeast extract, Hamilton Depression Scale (HDS) and Hamilton Anxiety Scale (HAS) were measured. HDS and HAS have been widely used as depression and anxiety valuation standard in neuropsychiatry. The lower scores of them represent the improvement of depression and anxiety. After each 10 patients with early depression and anxiety syndrome were administered with 200 mg of the present yeast extract (SCE) daily for 7 days, HDS and HAS were measured before and after the administration in order to identify the improvement of depression and anxiety (see FIGS. 17 and 18). To exclude the placebo effect, the control group administered with placebo without SCE was assayed for HDS and HAS using the same method. The resulting data are summarized in below Table 10.

TABLE 10

Change of HDS and HAS averages in SCE group and Placebo group

| | Group | | | | | | | |
| --- | --- | --- | --- | --- | --- | --- | --- | --- |
| | SCE group | | | | Placebo group | | | |
| Assay | | | | | | | | |
| | HDS | | HAS | | HDS | | HAS | |
| | Before | After | Before | After | Before | After | Before | After |
| Score | 18.5 | 14.8 | 20.1 | 15.6 | 12.7 | 10.6 | 11.4 | 8.6 |
| Change | 3.7 | | 4.5 | | 2.1 | | 2.8 | |

As seen in the above Table 10, HDS score was reduced in amount of 3.7 for SCE group representing improvement, whereas reduced in amount of 2.1 for Placebo group. Further, HAS score was reduced in amount of 4.5 for SCE group representing improvement, whereas reduced in amount of 2.8 for Placebo group.

Experimental Example 16

Clinical Test with Functional Gum

With the functional gum prepared in the above Example 3, anti-depression and anti-anxiety effects were tested on normal persons. Sixty six (66) volunteer normal persons were randomly divided into two groups. One group (33) was subjected to chewing gum comprising the present yeast extract (SCE) 30 mg, whereas the other group (33) was subjected to chewing gum without SCE for 2 weeks. After that, each level of depression and anxiety was assayed using BDI (Beck Depression Inventory) and BAI (Beck Anxiety Inventory). The resulting data was summarized in below Table 11.

TABLE 11

Anti-depression and anti-anxiety effects of functional gum with or without SCE

| | BDI(before) − BDI(after) | | BAI(before) − BAI(after) | |
| --- | --- | --- | --- | --- |
| Group | Mean | SD | Mean | SD |
| Control | 0.85 | 3.75 | 2.00 | 3.94 |
| SCE | 2.82 | 3.92 | 3.30 | 4.41 |

As shown in the Table 11, both of BDI and BAI were significantly reduced in SCE group, compared to Control group. Therefore, the functional gum of the present invention has an effect on improving depression and anxiety.

Experimental Example 17

Clinical Test with Edible Film

With the edible film prepared in the above Example 4, anti-depression and anti-anxiety effects were tested on normal persons. Sixty volunteer normal persons were randomly divided into three groups. One group (20) was subjected to taking an edible film comprising the present yeast extract (SCE) 3 mg per one film, another group (20) was subjected to taking an edible film comprising the present yeast extract (SCE) 10 mg per one film, and the other group (20) was subjected to taking an edible film without SCE for 2 weeks. After that, each level of depression and anxiety was assayed using BDI (Beck Depression Inventory) and BAI (Beck Anxiety Inventory). The resulting data was summarized in below Table 12.

TABLE 12

Anti-depression and anti-anxiety effects of edible film with or without SCE

| Group | BDI(before) – BDI(after) | | BAI(before) – BAI(after) | |
|---|---|---|---|---|
| | Mean | SD | Mean | SD |
| Control | 0.85 | 3.75 | 2.00 | 3.94 |
| SCE (3 mg) | 1.92 | 3.91 | 2.74 | 4.12 |
| SCE (10 mg) | 2.75 | 3.89 | 3.29 | 4.31 |

As shown in the Table 12, both of BDI and BAI were significantly reduced in SCE group, especially SCE group (10 mg), compared to Control group. Therefore, the edible film of the present invention has an effect on improving depression and anxiety.

Experimental Example 18

In Vivo Test for Anti-Obesity Effect

To test for anti-obesity effect of the present yeast extract, weight-reducing effect of the present yeast extract (SCE) was measured in high fat diet rats. For the present experiment, 7 week (190-195 g) of Sprague-Dawley rats were used. Before the experiment, 32 rats were provided with general feed and divided into 4 groups having the same average weight. After that, they were provided with high fat diet feed (about 500 kcal) for 12 days. For 12 days, each experimental group was orally administered daily with 1 g SCE/kg weight, whereas control group was administered with saline. The resulting data was summarized in below Table 13.

TABLE 13

Anti-obesity effect of the present yeast extract (SCE) in high fat diet rats

| Group | Body weight (g) | | | Body weight gain | | |
|---|---|---|---|---|---|---|
| | Begin | After 12 days | 12 days(g) | g/day | P |
| Control | 205.9 ± 0.93 | 300.5 ± 4.92 | 94.60 ± 5.01 | 7.88 ± 0.41 | |
| SCE | 202.3 ± 2.91 | 283.0 ± 4.18 | 80.73 ± 2.27 | 6.73 ± 0.19 | 0.03 |

Value: mean ± SE

As shown in the Table 13, weight increase of SCE group was significantly reduced, compared to Control group.

As described above, the present yeast extract has an activity of selectively inhibiting reuptake of serotonin and norepinephrine, and therefore, can be effectively used in preventing or treating various diseases related to reuptake of serotonin and norepinephrine, especially depression, anxiety, stress, fatigue and obesity. The present yeast extract can be used as an active ingredient in preparing pharmaceutical compositions or functional foods for preventing or treating the above diseases The present invention discloses new uses of yeast extract, which previously had solely been used as a food source, as an anti-stress agent and a neurotrophin. The yeast extract according to the present invention has applications as a substitute for conventional psychomimetics that have a number of side effects and as an active food source.

Instead of using a conventional complicated process of gene-recombinant strain expression, natural neurotrophins can be easily prepared from yeast-derived peptides obtained by the hydrolysis of good-grade yeast. Neurotrophins according to the present invention are prepared such that they pass through the brain blood barrier even when orally administered. The new development of uses of the yeast extract according to the present invention includes its uses as a medicine source for an anti-stress agent, an anti-stress agent, and a natural neurotrophin, as well as an active food source.

Conventionally, medicines containing, for example, serotonin or melatonin, have been administered to alleviate PMS or menstrual pains with the prescription of doctors or pharmacists. However, the yeast extract or yeast-derived peptides according to the present invention are prepared from a safe food source that effects no resistance or side effects and thus can be conveniently purchased and taken without a doctors' or pharmacists' prescription to relieve normal women of their monthly PMS or menstrual pain suffering.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treating a disorder comprising
administering to an animal having a disorder an amount of a yeast extract effective in treating the disorder,
wherein the disorder is clinical depression, anxiety, stress, or fatigue,
wherein the disorder is caused by excessive reuptake of serotonin and norepinephrine.

2. The method according to claim 1, wherein the yeast extract is prepared by autolyzing at a temperature of about 35-70° C. and/or hydrolyzing with a protease.

3. The method according to claim 1, wherein the yeast extract is administered in the form of a pharmaceutical composition or a functional food comprising the yeast extract as an active component.

4. The method of claim 3, wherein the functional food is a beverage, a gum, or an edible film.

5. The method of claim 3, wherein the pharmaceutical composition comprises a powder, a granule, an injectable form, a capsule, or a tablet.

6. The method of claim 1, wherein the disorder is clinical depression and the amount of yeast extract is 10 to 500 mg per day for an adult.

* * * * *